US008846096B2

(12) United States Patent
Destache

(10) Patent No.: US 8,846,096 B2
(45) Date of Patent: Sep. 30, 2014

(54) NANOPARTICLES AND METHODS OF USE

(75) Inventor: Christopher J. Destache, Omaha, NE (US)

(73) Assignee: Creighton University, Omaha, NE (US)

( * ) Notice: Subject to any disclaimer, the term of this patent is extended or adjusted under 35 U.S.C. 154(b) by 45 days.

(21) Appl. No.: 13/132,442

(22) PCT Filed: Dec. 11, 2009

(86) PCT No.: PCT/US2009/067724
§ 371 (c)(1),
(2), (4) Date: Jun. 2, 2011

(87) PCT Pub. No.: WO2010/068899
PCT Pub. Date: Jun. 17, 2010

(65) Prior Publication Data
US 2011/0236437 A1 Sep. 29, 2011

Related U.S. Application Data

(60) Provisional application No. 61/122,139, filed on Dec. 12, 2008.

(51) Int. Cl.
| A61K 9/14 | (2006.01) |
| A61K 9/00 | (2006.01) |
| B82Y 5/00 | (2011.01) |
| A61K 31/513 | (2006.01) |
| A61K 31/536 | (2006.01) |
| A61K 9/51 | (2006.01) |
| A61K 31/427 | (2006.01) |

(52) U.S. Cl.
CPC ............ *A61K 31/427* (2013.01); *A61K 9/0019* (2013.01); *B82Y 5/00* (2013.01); *A61K 9/14* (2013.01); *A61K 31/513* (2013.01); *A61K 31/536* (2013.01); *A61K 9/5153* (2013.01); *Y10S 977/773* (2013.01)
USPC .......................................... 424/489; 977/773

(58) Field of Classification Search
None
See application file for complete search history.

(56) References Cited

U.S. PATENT DOCUMENTS

| 7,056,532 | B1* | 6/2006 | Kabanov et al. .............. 424/486 |
| 2005/0048002 | A1 | 3/2005 | Rabinow et al. | |
| 2005/0130128 | A1 | 6/2005 | Ikezu et al. | |
| 2005/0202094 | A1* | 9/2005 | Werling et al. .............. 424/489 |
| 2008/0070920 | A1* | 3/2008 | Guo et al. .................. 514/252.02 |
| 2009/0061010 | A1 | 3/2009 | Zale et al. | |
| 2009/0252757 | A1 | 10/2009 | Nguyen et al. | |

FOREIGN PATENT DOCUMENTS

| EP | 1 611 878 A1 | 1/1998 |
| WO | WO 98/47492 A1 | 10/1998 |
| WO | WO 2005/072706 A2 | 8/2005 |
| WO | WO 2005/072706 A3 | 11/2005 |

OTHER PUBLICATIONS

CJ Destache, T Belgum, K Christensen, A Shibata. ("Ritonavir-, Lopinavir-, and Efavirenz-containing Nanoparticles: in vitro Release of Anti-Retroviral Therapy (ART)," (Abstract F-128 and poster), 8th Conference on Retrovirus and Opportunistic Infections, Feb, 3-6, 2008. Boston, Massachusetts.*
T Musumeci, CA Ventura, I Giannone, B Ruozi, L Montenegro, R Pignatello, G Puglisi. "PLA/PLGA nanoparticles for sustained release of docetaxel." International Journal of Pharmaceutics, vol. 325, 2006, pp. 172-179.*
YC Kuo, FL Su. "Transport of stavudine, delavirdine, and saquinavir across the blood-brain barrier by polybutylcyanoacrylate, methylmethacrylate-sulfopropylmethacrylate, and solid lipid nanoparticles." International Journal of Pharmaceutics, vol. 340, 2007, pp. 143-152, available online Mar. 12, 2007.*
YC Kuo, TW Lin. "Electrophoretic Mobility, Zeta Potential, and Fixed Charge Density of Bovine Knee Chondrocytes, Methyl Methacrylate-Sulfopropyl Methacrylate, Polybutylcyanoacrylate, and Solid Lipid Nanoparticles." Journal of Physical Chemistry B, vol. 110, 2006, pp. 2202-2208.*
Anabwani et al., "Nutrition and HIV/AIDS in sub-Saharan Africa: an overview," *Nutrition*, 2005; 21(1): 96-9.
Astete et al., "Synthesis and characterization of PLGA nanoparticles," *J. Biomater. Sci. Polymer Edn.*, 2006; 17(3): 247-89.
Beck et al., "I. Influence of polybutylcyanoacrylate nanoparticles and liposomes on the efficacy and toxicity of anticancer drug mitoxantrone in murine tumour models," *J. Microencapsul.*, Jan.-Mar. 1993; 10(1): 101-14.
Beck et al., "Improved peroral delivery of avoral with polybutylcyanoacrylate nanoparticles," *Eur. J. Pharm. Biopharm.*, 1994; 40(3): 134-7.
Bender et al., "Efficiency of Nanoparticles as a Carrier System for Antiviral Agents in Human Immunodeficiency Virus-Infected Human Monocytes/ Macrophages In Vitro," *Antimicrob. Agents Chemother.*, Jun. 1996; 40(6): 1467-71.

(Continued)

*Primary Examiner* — Frederick Krass
*Assistant Examiner* — Isaac Shomer
(74) *Attorney, Agent, or Firm* — Advent, LLP

(57) ABSTRACT

Provided herein are nanoparticles and methods for using nanoparticles. The nanoparticles include at least three antiretroviral agents. When introduced to cells the nanoparticles cause an increase in the intracellular concentration of the antiretroviral agents to a level that is at least the IC50 against HIV-I or HIV-2. This concentration may be maintained for at least 21 days after the cells are contacted with the nanoparticle. When administered to a subject the nanoparticles cause the concentration of the antiretroviral agents to increase to at least 100 ng/ml in the serum of the subject, at least 0.5 μg/gram tissue in an organ of the subject, or a combination thereof. Such a concentration may be maintained for at least 21 days after the administration.

4 Claims, 7 Drawing Sheets

(56) References Cited

OTHER PUBLICATIONS

Brannon-Pepas et al., "Nanoparticle and targeted systems for cancer therapy," *Adv. Drug Del. Rev.*, Sep. 22, 2004; 56(11): 1649-59.

Carlson et al., "Proteomic fingerprinting of HIV-1-infected human monocyte-derived macrophages: a preliminary report," *J Neuroimmunol.*, Feb. 2004; 147(1-2): 35-42.

Chan, "Bionanotechnology progress and advances," *Biol. Blood Marrow Transplant*, Jan. 2006; 12(1 Suppl. 1): 87-91.

Chattopadhyay et al., "Solid lipid nanoparticles enhance the delivery of the HIV protease inhibitor, atazanavir, by a human brain endothelial cell line," *Pharm. Res.*, Oct. 2008; 25(10): 2262-71.

Chen et al., "Immunologic and virologic consequences of temporary antiretroviral treatment interruption in clinical practice," *AIDS Res. Hum. Retroviruses*, Sep. 1, 2002; 18(13): 909-916.

Chulamokha et al., "Antiretroviral therapy in the developing world," *J. Neurovirol.*, 2005; 11(Suppl. 1): 76-80.

Chun et al., "Re-emergence of HIV after stopping therapy," *Nature*, Oct. 28, 1999; 401(6756): 874-5.

Chun et al., "Persistence of HIV in Gut-Associated Lymphoid Tissue despite Long-Term Antiretroviral Therapy," *J. Infect. Dis.*, Mar. 1, 2008; 197(5): 714-20.

Clements, "The central nervous system is a viral reservoir in simian immunodeficiency virus-infected macaques on combined antiretroviral therapy: a model for human immunodeficiency virus patients on highly active antiretroviral therapy," *J. Neurovirol.*, Apr. 2005; 11(2): 180-9.

Conway et al., "Protection against Bordetella pertussis infection following parenteral or oral immunization with antigens entrapped in biodegradable particles: effect of formulation and route of immunization on induction of $Th_1$ and $Th_2$ cells," *Vaccine*, Feb. 28, 2001; 19(15-16): 1940-50.

Couvreur et al., "Toxicity of polyalkylcyanoacrylate nanoparticles II: Doxorubicin-loaded nanoparticles," *J. Pharm. Sci.*, Jul. 1982; 71(7): 790-2.

Denizot et al., "Rapid colorimetric assay for cell growth and survival. Modifications to the tetrazolium dye procedure giving improved sensitivity and reliability," *J. Immunol. Methods*, May 22, 1986; 89(2): 271-7.

Destache et al., "Ritonavir-, Lopinavir-, and Efavirenz-conthining Nanoparticles: in vitro Release of Anti-Retroviral Therapy (ART)," (Abstract F-128 and poster). 8th *Conference on Retrovirus and Opportunistic Infections*, Feb. 3-6, 2008. Boston, Massachusetts.

Destache et al. In vivo levels of ritonavir (RTV), lopinavir (LPV), efavirenz (EFC) over time after intraperitoneal (IP) injection of antiretroviral (AR) PLGA nanoparticle (NP). Abstract A1-1313 and poster). 49th Interconference on Antimicrobial Agents and Chemotherapy. San Francisco, CA. Sep. 12-15, 2009.

Destache, Chris, "Pharmacology of Antiretroviral Nanoparticle Micelles," Grant Abstract of Grant Submission that became Grant No. 1R15A1076039-01A1 upon granting, project dates: 2008-2010, 1 pg.

Destache et al. "Combination antiretroviral drugs in PLGA nanoparticle for HIV-I," Research Article. *BMC Infectious Diseases*. 2009. 9:198. 8 pages.

Destache et al. "Antiretroviral release from ply(DL-lactide-co-glycolide) nanoparticles in mice," *J. Antimicrob Chemother.* 2010. 65:2183-2187.

Destache et al. "Chapter 12—Brain as an HIV sequestered site: Use of nanoparticles as a therapeutic option". 2009. *Prog. Brain Res.* 180:225-33.

Dou et al., "Development of a macrophage-based nanoparticle platform for antiretroviral drug delivery," *Blood*, Oct. 15, 2006; 108(8): 2827-2835.

Dou et al., "Laboratory investigations for the morphologic, pharmacokinetic, and anti-retroviral properties of indinavir nanoparticles in human monocyte-derived macrophages," *Virology*, Feb. 5, 2007; 358(1): 148-58.

Dou et al. "Macrophage delivery of nanoformulated antiretroviral drug to the brain in a murine model of neuroAIDS." 2009. *J. Immunol.* 1:183(1):661-9. Epub Jun. 17, 2009. PubMed PMID: 19535632. PubMed Central PMCID: PMC2765254.

Eley et al., "Poly (lactide-co-glycolide) nanoparticles containing coumarin-6 for suppository delivery: in vitro release profile and in vivo tissue distribution," *Drug. Deliv.*, Jul.-Aug. 2004; 11(4): 255-61.

Farmer et al., "Community-based treatment of advanced HIV disease: introducing DOT-HAART (directly observed therapy with highly active antiretroviral therapy)," *Bull. World Health Organ.*, 2001; 79(12): 1145-51.

Fellay et al., "Prevalence of adverse events associated with potent antiretroviral treatment: Swiss HIV Cohort Study," *Lancet*, Oct. 20, 2001; 358(9290): 1322-7.

Fellay et al., Errata to "Prevalence of adverse events associated with potent antiretroviral treatment: Swiss HIV Cohort Study," *Lancet*, Dec. 15, 2001; 358(9298): 2088.

Gagne et al., "Targeted delivery of indinavir to HIV-1 primary reservoirs with immunoliposomes," *Biochim. Biophy. Acta*, Feb. 1, 2002; 1558(2): 198-210.

Gartner et al., "The role of mononuclear phagocytes in HTLV-III/LAV infection," *Science*, Jul. 11, 1986; 233(4760): 215-9.

Gorantla et al., "Quantitative magnetic resonance and SPECT imaging for macrophage tissue migration and nanoformulated drug delivery," *J. Leukoc. Biol.*, Nov. 2006; 80(5): 1165-74.

Govender et al., "Polymeric Nanoparticles for Enhancing Antiretroviral Drug Therapy," *Drug Delivery*, Nov. 2008; 15(8) 493-501.

Hansen et al., "Re-examination and further development of a precise and rapid dye method for measuring cell growth/cell kill," *J. Immunol. Methods*, May 12, 1989; 119(2): 203-10.

International Search Report of the International Searching Authority, issued Mar. 11, 2010, for Patent Application No. PCT/US2009/067724, filed Nov. 12, 2009. 5 pgs. total.

Kingsley et al., "Nanotechnology: A Focus on Nanoparticles as a Drug Delivery System," *J. Neuroimmun. Pharmacol.*, Sep. 2006; 1(3): 340-50.

Kreuter, "Nanoparticles," In: *Colloidal Drug Delivery Systems*. Edited by Kreuter, New York; 1994: 219-342.

Kuhnel et al., "Molecular cloning of two Wet African human immunodeficiency virus type 2 isolates that replicate well in macrophages: a Gambian isolate, from a patient with neurologic acquired immunodeficiency syndrome, and a highly divergent Ghanian isolate," *Proc. Natl. Acad. Sci. USA*, Apr. 1989; 86(7): 2382-7.

Kuo, "Loading efficiency of stavudine on polybutylcyanoacrylate and methylmethacrylate-sulfopropylmethacrylate copolymer nanoparticles," *Int. J. Pharmaceut.*, Feb. 2005; 290(1-2): 161-72.

Kuo et al., "Transport of stavudine, delavirdine, and saquinavir across the blood-brain barrier by polybutylcyanoacrylate, methylmethacrylate-sulfopropylmethacrylate, and solid lipid nanoparticles," *Int. J Pharmaceut.*, 2007; 340(1-2): 143-52.

Mainardes et al., "Zidovudine-loaded PLA and PLA-PEG blend nanoparticles: influence of polymer type on phagocytic uptake by polymorphonuclear cells," *J. Pharm. Sci.*, Jan. 2009; 98(1): 257-67.

McGann et al., "Human immunodeficiency virus type 1 causes productive infection of macrophages in primary placental cell cultures," *J. Infect. Dis.*, Apr. 1994; 169(4): 746-53.

Milman et al., "Mechanisms of HIV/SIV mucosal transmission," *AIDS Res. Hum. Retroviruses*, Oct. 1994; 10(10): 1305-12.

Nataraj an et al., "HIV-1 replication in patients with undetectable plasma virus receiving HAART. Highly active antiretroviral therapy," *Lancet*, Jan. 1999; 353(9147): 119-20.

Nicholson et at, "In vitro infection of human monocytes with human T lymphotropic virus type III/lymphadenopathy-associated virus (HTLV-III/LAV)," *J. Immunol.*, Jul. 1, 1986; 137(1): 323-9.

Palepu et al., "Antiretroviral adherence and HIV treatment outcomes among HIV/HCV co-infected injection drug users: the role of methadone maintenance therapy," *Drug Alcohol Depend.*, Sep. 15, 2006; 84(2): 188-94.

Piot et al., "The global impact of HIV/AIDS," *Nature*, Apr. 19, 2001; 410: 968-73.

(56) References Cited

OTHER PUBLICATIONS

Ramratnam et al., "Intensification of antiretroviral therapy accelerates the decay of the HIV-1 latent reservoir and decreases, but does not eliminate, ongoing virus replication," *J.Acquir. Immune Defic. Syndr.*, Jan. 1, 2004; 35(1): 33-7.

Rao et al. "Biodegradable PLGA Based Nanoparticles for Sustained Regional Lymphatic Drug Delivery," 2009. Journal of Pharmaceutical Sciences. pp. 1-14.

Rockstroh et al., "Adherence to enfuvirtide and its impact on treatment efficacy," A*IDS Res. Hum. Retroviruses*, Feb. 2008; 24(2): 141-8.

Sengupta et al., "Temporal targeting of tumour cells and neovasculature with a nanoscale delivery system," *Nature*, Jul. 28, 2005; 436(7050): 568-72.

Shah et al., "Intracellular delivery of saquinavir in biodegradable polymeric nanoparticles for HIV/AIDS," *Pharm. Res.*, Nov. 2006; 23(11): 2638-45.

Shenoy et al., "Poly(ethylene oxide)-modified poly(beta—amino ester) nanoparticles as a pH-sensitive system for tumor-targeted delivery of hydrophobic drugs: part 2. In vivo distribution and tumor localization studies," *Pharm Res.*, Dec. 2005; 22(12): 2107-14.

Van t'Klooster et al., "Pharmacokinetics and Disposition of Rilpivirine (TMC278) Nanosuspension as a Long-Acting Injectable Antiretroviral Formulation." *Antimicrobial Agents and Chemotherapy*. 2010. 54(5):2042-2050.

Varshosaz et al., "Production and in vitro characterization of lisinopril-loaded nanoparticles for the treatment of restenosis in stented coronary arteries," *J. Microencapsul.*, Oct. 2008; 25(7): 478-86.

von Briesen et al., "Infection of monocytes/macrophages by HIV in vitro," *Res Virol*, Mar.-Apr. 1990; 141(2): 225-31.

Weller et al., "An isocratic liquid chromatography method for determining HIV non-nucleoside reverse transcriptase inhibitor and protease inhibitor concentrations in human plasma," *J. Chromatrogr. B. Analyt. Technol. Biomed. Life Sci.*, Apr. 1, 2007; 848(2): 369-73.

Written Opinion of the International Searching Authority, issued Nov. 3, 2010, for Patent Application No. PCT/US2009/067724, filed Nov. 12, 2009.

Zhang et al., "Quantifying residual HIV-1 replication in patients receiving combination antiretroviral therapy," *N. Engl. J. Med.*, May 27, 1999; 340(21): 1605-13.

Zhang et al., "In vitro and in vivo investigation on PLA-TPGS nanoparticles for controlled and sustained small molecule chemotherapy," *Pharm. Res.*, Aug. 2008; 25(8): 1925-35.

\* cited by examiner

NANOPARTICLES AND METHODS OF USE

This application is the §371 U.S. National Stage of International Application No. PCT/US2009/067724, filed Dec. 11,2009, which claims the benefit of U.S. Provisional Application Ser. No. 61/122,139 filed Dec. 12, 2008, which are incorporated by reference herein.

GOVERNMENT FUNDING

The present invention was made with government support under Grant No. 1R15AI076039-01A1, awarded by the NIH. The Government has certain rights in this invention.

BACKGROUND

An estimated 39 million people are infected with human immunodeficiency type-1 (HIV-1) world-wide (Piot et al., Nature, 2001, 410:968-973). The majority of infected people live in the developing world with limited treatment resources. Antiretroviral therapy (ART) has significantly reduced HIV-1 disease morbidity and improved life expectancy. However, a number of factors make eradication of HIV-1 by antiretroviral therapy more difficult. These include difficulties adhering to complex antiretroviral regimens of drugs with low margins for pharmacokinetic deviation, identification of cellular reservoirs that survive despite ART, and the potential existence of sanctuary sites within the body where antiretroviral drug levels are not optimal. Additionally, the economics of drug treatment, treatment failures due to the development of resistance, and limited global access has prevented world-wide use of antiretroviral therapy (Chen et al., AIDS Trd Hum Retroviruses, 2002, 18:900-916, Chulamokha et al., J. Neurovirol., 2005, 11:76-80). Dosing regimens that require multiple daily dosing with diet considerations and antiretroviral therapy side effects have compromised the achievement of longterm HIV-1 suppression in infected patients (Fellay et al., Lancet, 2001, 358:1322-1327).

The CD4+ T lymphocyte is the major target for infection by HIV-1. Cells of the mononuclear phagocyte system also serve as a reservoir for HIV. Macrophages are mature, non-proliferating and immunologically active cells that can be productively infected with HIV-1 and HIV-2 (Gartner et al., Science, 1986, 233:215-219, Kuhnel et al., Proc Natl Acad Sci USA, 1989, 86:2382-2387, Nicholson et al., J Immunol., 1986, 137:323-329, von Briesen et al., Res Virol., 1990, 141:225-231). Altered cellular functions in the macrophage population may contribute to the development and clinical progression of AIDS.

Evidence has accumulated that cells of the macrophage lineage are vectors for the transmission of HIV-1. The placental macrophage is likely to be the primary cell type responsible for vertical transmission of HIV-1 (McGann et al., J Infect Dis., 1994, 169:746-753). An important property of HIV-1 for mucosal transmission is the ability to infect macrophages (Milman et al., AIDS Res. Hum Retroviruses, 1994, 10:1305-1312). Because of the important role of cells of the monocytes/macrophage (Mo/Mac) lineage in the pathogenesis of HIV-1, fully effective antiretroviral therapy must react with Mo/Mac in addition to other targets.

Many promising compounds suffer from poor physiochemical properties leading to poor solubility and biodistribution. Such properties limit drug-receptor interactions to cause desired effects. For example, proteins and peptides could be new drug candidates but suffer from low oral absorption in the gastrointestinal tract.

Combination antiretroviral therapy has significantly reduced HIV-1 disease morbidity and improved life expectancy. Combinations of drugs from different classes have proven to offer sustained efficacy and long-term safety. Controlling viral replication allows at least partial reconstitution of the immune system. However, despite sustained viral suppression for prolonged periods, eradication of HIV-1 from patients has not been achieved.

SUMMARY OF THE INVENTION

There remains a need for compositions useful in the treatment of retroviral diseases, particularly compositions that do not require daily dosing regimens. Provided herein are methods for using nanoparticles. In one aspect, the method includes contacting a cell with an effective amount of a composition including nanoparticles under conditions suitable for uptake of the particles by the cell. The nanoparticles may have an average size of from 10 nanometers to 750 nanometers. The nanoparticles may include alginate, cellulose, polyhydroxyalkanoates, polyamides, polyphosphazenes, polypropylfumarates, polyethers, polyacetals, polycyanoacrylates, biodegradable polyurethanes, polycarbonates, polyanhydrides, polyhydroxyacids, poly(ortho esters), and/or polyesters, such as poly(lactic acid-co-glycolic acid) and poly(lactide-co-glycolide).

The cell may be a phagocytic cell, such as a macrophage, a monocyte, a monocyte-derived macrophage, a granulocyte, a neutrophil. The cell may be primate, such as human or monkey, or from a murine animal, such as a rat or mouse. The cell may be infected with a retrovirus, such as HIV-1, HIV-2, or SIV. The cell may be in vitro or ex vitro. The method may further include implanting the explanted cell into the subject from which it was explanted.

Each nanoparticle includes a mixture of at least three antiretroviral agents. The intracellular concentration of each antiretroviral agent may be at least the half maximal inhibitory concentration for a retrovirus present in the cells, such as HIV-1$_{ada}$. Such an intracellular concentration may be maintained for at least 21 days after the cells are contacted with the nanoparticles.

The antiretroviral agents may be a nucleoside reverse transcriptase inhibitor, a nucleotide reverse transcriptase inhibitor, a non-nucleoside reverse transcriptase inhibitor, a protease inhibitor, an integrase inhibitor, a fusion inhibitor, a maturation inhibitor, or a combination thereof. Examples of nucleoside reverse transcriptase inhibitors include zidovudine, didanosine, stavudine, zalcitabine, abacavir, emtricitabine, and lamivudine. Examples of non-nucleoside reverse transcriptase inhibitors include efavirenz, nevirapine, and delaviradine. Examples of protease inhibitors include indinavir, ritonavir, saquinavir, lopinavir, and nelfinavir. Examples of a reverse transcriptase inhibitor, an integrase inhibitor, a fusion inhibitor, and a maturation inhibitor are tenofovir, raltegravir, mariviroc, and bevirimat, respectively. In some aspects, the antiretroviral agents present in a nanoparticle include, ritonavir, lopinavir, and efavirenz, or efavirenz, abacavir, and lamivudine, or emtricitabine, tenofovir, and raltegravir.

In other aspects, the methods may be directed to increasing the concentration of an agent in a subject, or treating a condition in a subject. The methods may include administering to a subject an effective amount of a composition that includes nanoparticles described herein. A single administration may result in a concentration of at least one antiretroviral agent of at least 100 ng/ml in the serum of the subject, at least 0.5 µg/gram tissue in an organ of the subject (such as, but not limited to, testes, kidney, spleen, liver, and brain), or a combination thereof. Such a concentration may be maintained for at least 21 days after the administration. The condition may be an AIDS-related condition. The administration may be subcutaneous, intramuscular, or intraperitoneal. The subject may be infected with a retrovirus, such as HIV-1 or HIV-2, and the infection may be inhibited.

The present invention is also directed to nanoparticles that includes at least three antiretroviral agents, and compositions thereof. The average size of the nanoparticles may be from 10 nanometers to 750 nanometers. The nanoparticles may have a surface charge of between −40 mV and −2 mV. The nanoparticles may include alginate, cellulose, polyhydroxyalkanoates, polyamides, polyphosphazenes, polypropylfumarates, polyethers, polyacetals, polycyanoacrylates, biodegradable polyurethanes, polycarbonates, polyanhydrides, polyhydroxyacids, poly(ortho esters), and/or polyesters, such as poly(lactic acid-co-glycolic acid) and poly(lactide-co-glycolide).

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4,0 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
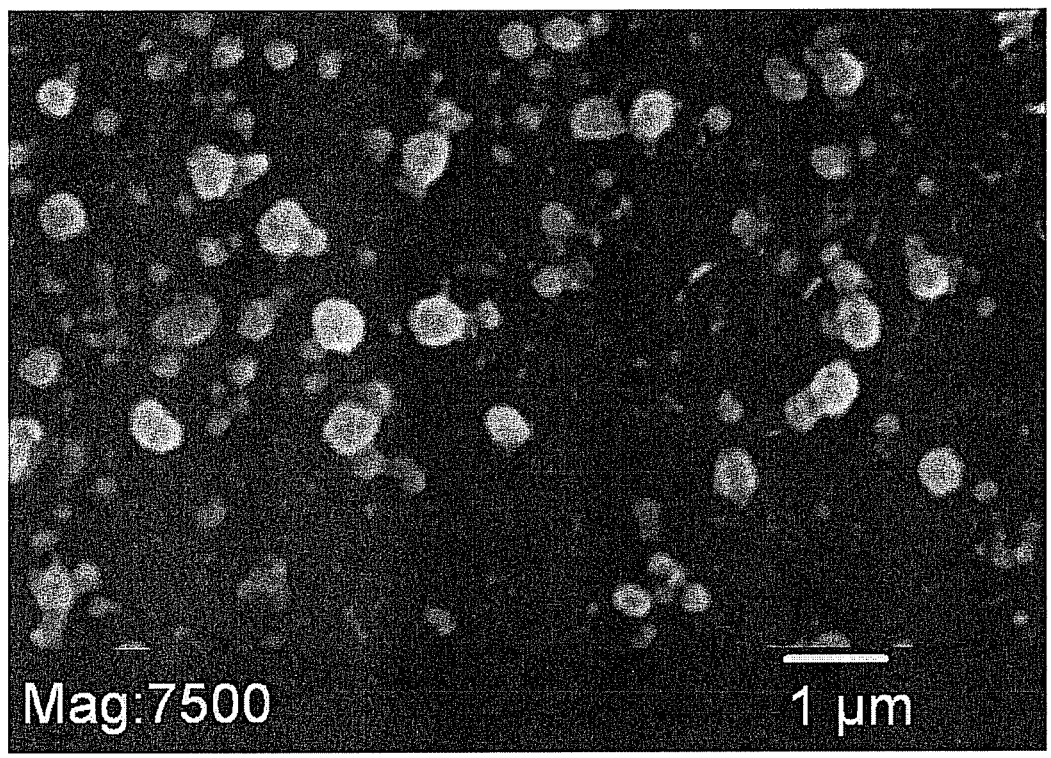
FIG. 1. Scanning electron microscopy (SEM) of fabricated antiretroviral nanoparticles (Mag×7500).

The invention provided herein is predicated in part on the discoveries by the present inventors of methods for using nanoparticles to increase the concentration of agents in organs and serum for extended periods of time. The expectation was introduction of nanoparticles into a subject would result in storage of the nanoparticles in organs such as liver and spleen, and an increase in the concentration of any agent associated with the nanoparticles in these organs. An increase in the serum concentration of a nanoparticle-associated agent was not expected. In contrast, as detailed in the Examples below, the introduction to animals of nanoparticles containing three antiretroviral agents resulted in sustained levels of the drugs in organs and serum for greater than 28 days.

Provided herein are particles (also referred to herein as nanoparticle(s)). As used herein, the term "particle" and "nanoparticle" refer to particles between 10 and 1000 nanometers (nm) in diameter. For instance, the diameter of a nanoparticle may be at least 10 nm, at least 50 nm, at least 100 nm, or at least 150 nm, and may be no greater than 700 nm, no greater than 650 nm, or no greater than 600 nm. A numerical value for diameter of a nanoparticle may include a range of +/−0.10% of the stated value.

A particle includes one or more polymers. A "polymer," as used herein, is given its ordinary meaning as used in the art, i.e., a molecular structure including one or more repeat units (monomers), connected by covalent bonds. The repeat units may all be identical, or in some cases, there may be more than one type of repeat unit present within the polymer. A polymer may be natural (e.g., biologically derived) or unnatural (e.g., synthetically derived). Polymers may be homopolymers or copolymers including two or more monomers. In teens of sequence, copolymers may be random, block, or include a combination of random and block sequences.

A wide variety of polymers and methods for fowling particles are known. In some aspects, the matrix of a particle includes one or more polymers. Any polymer may be used in accordance with the present invention. Polymers may be homopolymers or copolymers including two or more monomers. Copolymers may be random, block, or include a combination of random and block sequences.

If more than one type of repeat unit is present within the polymer, then the polymer is said to be a "copolymer." It is to be understood that in any aspect employing a polymer, the polymer may be a copolymer. The repeat units forming the copolymer may be arranged in any fashion. For example, the repeat units may be arranged in a random order, in an alternating order, or as a "block" copolymer, i.e., including one or more regions each including a first repeat unit (e.g., a first block), and one or more regions each including a second repeat unit (e.g., a second block), etc. Block copolymers may have two (a diblock copolymer), three (a triblock copolymer), or more numbers of distinct blocks.

A polymer may be biocompatible polymer, i.e., the polymer does not typically induce an adverse response when introduced into a living subject, for example, without significant inflammation and/or acute rejection of the polymer by the immune system, for instance, via a T-cell response. It will be recognized that "biocompatibility" is a relative term, and some degree of immune response is to be expected even for polymers that are highly compatible with living tissue. As used herein, "biocompatibility" refers to the acute rejection of material by at least a portion of the immune system, i.e., a non-biocompatible material introduced into a subject provokes an immune response in the subject that is severe enough such that the rejection of the material by the immune system cannot be adequately controlled, and often is of a degree such that the material must be removed from the subject. Non-limiting examples of biocompatible polymers that may be useful in various embodiments of the present invention include polydioxanone, polyhydroxyalkanoate, polyhydroxybutyrate, poly(glycerol sebacate), polyglycolide, polylactide, PLGA, polycaprolactone, or copolymers or derivatives including these and/or other polymers.

A polymer may be biodegradable, i.e., the polymer is able to degrade, chemically and/or biologically, within a physiological environment, such as within the body. For instance, the polymer may be one that hydrolyzes spontaneously upon exposure to water (e.g., within a subject), or degrades upon exposure to heat (e.g., at temperatures of 42° C.). Degradation of a polymer may occur at varying rates, depending on the polymer or copolymer used. For example, the half-life of the polymer (the time at which 50% of the polymer is degraded into monomers and/or other nonpolymeric moieties may be on the order of days or weeks, depending on the polymer. The polymers may be biologically degraded, e.g., by enzymatic activity or cellular machinery. In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

Examples of natural and synthetic polymers useful in the preparation of biodegradable microspheres include carbohydrates such as alginate, cellulose, polyhydroxyalkanoates, polyamides, polyphosphazenes, polypropylfumarates, polyethers, polyacetals, polycyanoacrylates, biodegradable polyurethanes, polycarbonates, polyanhydrides, polyhydroxyacids, poly(ortho esters), and polyesters. Examples of polyesters include copolymers including lactic acid and glycolic acid units, such as poly(lactic acid-co-glycolic acid) and poly(lactide-co-glycolide), collectively referred to herein as "PLGA"; and homopolymers including glycolic acid units, and lactic acid units, such as poly-L-lactic acid, poly-D-lactic acid, poly-D,L-lactic acid, poly-L-lactide, poly-D-lactide, and poly-D,L-lactide.

In some aspects a polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA to be used in accordance with the present invention is characterized by a lactic acid:glycolic acid ratio of 85:15, 75:25, 60:40, 50:50, 40:60, 25:75, or 15:85.

A nanoparticle described herein may have a surface charge that is positive or negative. For example, in those aspects where a nanoparticle has a negative surface charge, the surface charge may be at least −40 millivolts (mV), at least −35 mV, at least −30 mV, at least −25 mV, at least −20 mV, no greater than −10 mV, no greater than −15 mV, no greater than −20 mV, no greater than −25 mV, or any combination thereof. For instance, a nanoparticle may have a negative surface charge of at least −40 mV to no greater than −20 mV. In those aspects where a nanoparticle has a positive surface charge, the surface charge may be at least 2 millivolts (mV), at least 15 mV, at least 20 mV, at least 25 my, or at least 30 my, no greater than 40 mV, no greater than 35 mV, no greater than 30 mV, no greater than 25 mV, or any combination thereof.

A particle includes an agent. The term "agent" includes any substance, molecule, element, compound, entity, or a combination thereof. It includes, but is not limited to, polypeptide, small organic molecule, polysaccharide, polynucleotide, and the like. It can be a natural product, a synthetic compound, or a chemical compound, or a combination of two or more substances. Unless otherwise specified, the terms "agent," "substance," and "compound" can be used interchangeably. In some aspects, the agent may be associated with the surface of, encapsulated within, surrounded by, dissolved in, and/or dispersed throughout the polymeric matrix.

The agent may be a therapeutic agent. Examples of therapeutic agents include antiretroviral agents and anti-inflammatory agents. Examples of antiretroviral agents include, but are not limited to, nucleoside reverse transcriptase inhibitors, nucleotide reverse transcriptase inhibitors, non-nucleoside reverse transcriptase inhibitors, protease inhibitors, integrase inhibitors, fusion inhibitors, and maturation inhibitors. Non-limiting examples of nucleoside reverse transcriptase inhibitors include zidovudine, didanosine, stavudine, zalcitabine, abacavir, emtricitabine, and lamivudine. Non-limiting examples of nucleotide reverse transcriptase inhibitors include tenofovir. Non-limiting examples of non-nucleoside reverse transcriptase inhibitors include efavirenz, nevirapine, and delaviradine. Non-limiting examples of protease inhibitors include HIV protease inhibitors, such as indinavir, ritonavir, saquinavir, lopinavir, and nelfinavir. Non-limiting examples of integrase inhibitors include raltegravir. Non-limiting examples of fusion inhibitors include mariviroc. Non-limiting examples of maturation inhibitors include bevirimat. In some aspects, a particle may include 1, 2, 3, or more therapeutic agents.

The agent may be a diagnostic agent, such as a contrast agent, a radiolabeled agent (for instance, radionuclides, paramagnetic contrast agents, β-emitters), a fluorescent agent, a luminescent agent, or a magnetic agent.

Therapeutic agents and diagnostic agents are known in the art (Physicians' Desk Reference, and Rabinow et al., U.S. Patent Application 20050048002) and are commercially available or can be prepared using routine methods known to the skilled person. A particle may include both therapeutic and diagnostic agents. The amount of each agent present in a particle (drug load) may be at least 0.1%, at least 0.5%, at least 1%, at least 5%, at least 10%, at least 15%, at least 20%, or at least 25% by weight.

A particle may include a targeting molecule. A targeting molecule is able to bind to a biological entity, such as a membrane component or a cell surface receptor. For instance, a targeting molecule may increase the interaction of a particle with a macrophage and/or monocyte. Useful targeting molecules may bind to, for example, tenascin C, tissue factor, tissue inhibitor of MMP 1 and 2, CD36, heme oxygenase-1, human cartilage gp-39, IL-6, IL-6 receptor, IL-10, IL-10 receptor, LOX-1, bacterial chemotactic peptide receptor agonists, such as Formyl-Methionine-Leucine-Phenylalanine ("F-MLP"), macrophage chemoattractant protein-1 receptor ("CCR-9") and monocyte inflammatory protein-1 and receptors thereof (including "CCR-5"). Such molecular carriers can be, for example, antibodies against these molecules, ligands binding the same, or analogs thereof. Other targeting molecules may increase the movement of a particle into the central nervous system. While targeting may be desirable in some aspects, the skilled person will recognize that targeting some agents will concentrate the agents and possibly result in side effects and/or toxicity. In those aspects where a particle includes a targeting molecule, the targeting molecule typically does not function to exclude the particle from non-targeted sites.

Compositions

The present invention is also directed to compositions including a particle described herein. Such compositions typically include a pharmaceutically acceptable carrier. As used herein "pharmaceutically acceptable carrier" includes saline, solvents, dispersion media, coatings, antibacterial and antifungal agents, isotonic and absorption delaying agents, and the like, compatible with pharmaceutical administration. Additional active compounds can also be incorporated into the compositions.

A composition may be prepared by methods well known in the art of pharmaceutics. In general, a composition can be formulated to be compatible with its intended route of administration. Examples of routes of administration include perfusion, oral, mucosal (e.g., nasal, sublingual, vaginal, buccal, or rectal), parenteral (e.g., subcutaneous, intravenous, bolus injection, intramuscular, or intraaterial), or transdermal administration. Solutions or suspensions can include the following components: a sterile diluent such as water for administration, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates; electrolytes, such as sodium ion, chloride ion, potassium ion, calcium ion, and magnesium ion, and agents for the adjustment of tonicity such as sodium chloride or dextrose. pH can be adjusted with acids or bases, such as hydrochloric acid or sodium hydroxide. A composition can be enclosed in ampoules, disposable syringes or multiple dose vials made of glass or plastic.

Compositions can include sterile aqueous solutions (where water soluble) or dispersions and sterile powders for the extemporaneous preparation of sterile solutions or dispersions. For intravenous administration, suitable carriers include physiological saline, bacteriostatic water, Cremophor EL™ (BASF, Parsippany, N.J.) or phosphate buffered saline (PBS). A composition is typically sterile and, when suitable for injectable use, should be fluid to the extent that easy syringability exists. It should be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition.

Sterile solutions can be prepared by incorporating the active compound (i.e., a particle described herein) in the required amount in an appropriate solvent with one or a combination of ingredients enumerated above, as required, followed by sterilization. Generally, dispersions are prepared by incorporating the active compound into a sterile vehicle, which contains a basic dispersion medium and any other appropriate ingredients. In the case of sterile powders for the preparation of sterile injectable solutions, preferred methods of preparation include vacuum drying and freeze-drying which yields a powder of the active ingredient plus any additional desired ingredient from a previously sterilized solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The concentration of particles in a composition may be selected as the amount necessary to deliver a desired amount of an active agent to the subject, and in accordance with the particular mode of administration selected. Toxicity and minimal inhibitory concentrations of such active compounds may be known, or may be determined by standard pharmaceutical procedures in cell cultures or experimental animals, e.g., for determining the $IC_{50}$ (the 50% inhibitory concentration).

The data obtained from cell culture assays and animal studies can be used in formulating a range of dosage for use in humans. The dosage of such compounds lies preferably within a range of circulating concentrations that are above the $IC_{50}$ with little or no toxicity. The dosage may vary within this range depending upon the dosage form employed and the route of administration used. For an agent used in the methods of the invention, the therapeutically effective dose may be estimated initially from cell culture assays to evaluate agent release from the particles. Such assays may include human monocytes, macrophages, T-cells, and/or peripheral blood mononuclear cells infected with a retrovirus, e.g., $HIV-1_{ada}$. A dose may be formulated in animal models (such as mouse, rat, or monkey) to achieve a circulating plasma concentration range that is above the $IC_{50}$ (i.e., the concentration of the agent that inhibits 50% of the growth of virus) as determined in cell culture. Such information can be used to more accurately determine useful doses in humans. Levels in serum may be measured, for example, by high performance liquid chromatography. Except under certain circumstances when higher dosages may be required, the preferred dosage of an HIV-inhibiting agent is within the range that results in a serum concentration that is at least the $IC_{50}$ for each agent.

The compositions can be administered one or more times per week to one or more times per month. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with an effective amount of a polypeptide can include a single treatment or, preferably, can include a series of treatments.

The particles may each be substantially the same shape and/or size ("monodisperse"). For example, the particles may have a distribution of characteristic dimensions such that no more than 5% or 10% of the particles have a characteristic dimension greater than 10% greater than the average characteristic dimension of the particles, and in some cases, such that no more than 8%, 5%, 3%, 1%, 0.3%, 0.1%, 0.03%, or 0.01% have a characteristic dimension greater than 10% greater than the average characteristic dimension of the particles.

Methods of Making

The particles described herein may be made using numerous techniques known to those skilled in the art. Examples of methods include, but are not limited to, emulsion or microemulsion polymerization, interfacial polymerization, precipitation polymerization, emulsion evaporation (such as oil in water emulsions, water in oil emulsions, and water in oil in water double emulsions), emulsion diffusion, solvent displacement, salting out, and the like. Parameters that can be varied may include, but are not limited to, polymer concentration, co-polymer ratio, polymer molecular mass, surfactant concentration, solvent used, phase volume ratio, and the like.

In one aspect the method for making particles includes a double emulsion (water in oil in water). A multiphase system may be used, including a first aqueous phase, an organic phase that includes the agent to be incorporated into the nanoparticle, and a second aqueous phase. The first aqueous phase typically includes an emulsifier, such as polyvinyl alcohol at 0.25% (w/v). The second aqueous phase may include a polyoxyethylene-polyoxypropylene copolymer (poloxamer), for instance, ethylene oxide/propylene oxide block copolymer, dissolved in water at a concentration of 2% (w/v). The molecular mass of the polyoxypropylene core may be 2,700 g/mol, and the percentage polyoxyethylene content may be 70%. Such a polymer is sold under the tradename POLOXAMER, for instance, Poloxamer-127 or Pluronic F-127. The organic phase includes an organic solvent and poly-lactic-co-glycolic acid (PLGA) polymer at a concentration of at least 1 mg PLGA/ml organic solvent. The lactic acid-glycolic acid ratio of the PLGA polymer may be 50:50. Examples of suitable organic solvents include methylene chloride and ethyl acetate. In those aspects where the agent(s) to be included in the particle is hydrophobic, the agent may be dissolved in the organic phase. Each agent may be present in the organic phase at a concentration of at least 0.1 mg/ml (w/v) or at least 4 mg/ml.

In a typical procedure, the first aqueous phase is homogenized with the organic phase to form a water in oil emulsion. This emulsion is further emulsified into a second aqueous solution of a diblock co-polymer surfactant, such as Pluronic F127 at 0.25% (w/v). For example, 5 mls of the first aqueous phase are homogenized with 5 mls of the organic phase, and this emulsion is emulsified using 30 mls of the second aqueous phase. The organic solvent is typically evaporated, and then the resulting particles are washed to remove unentrapped agent and emulsifier. The dispersion may be further treated by, for instance, lyophilization. Particles can then be screened using routine methods to identify those particles having one or more desired properties, for example, morphology, surface functionality, surface charge, size, zeta potential, biocompatibility, and the like.

Methods of Use

Also provided herein are methods for using particles. In one aspect, the methods include delivering a particle to a cell. For instance, a method may include contacting a cell with an effective amount of a composition under conditions suitable for uptake of particles by the cell. As used herein, conditions that are "suitable" for an event to occur, such as the uptake of a particle by a cell, or "suitable" conditions are conditions that do not prevent such events from occurring. Thus, these conditions permit, enhance, facilitate, and/or are conducive to the event. The mechanism of uptake is not intended to be limiting. Accordingly, cellular uptake of the particles may include endocytosis, such as phagocytosis or pinocytosis, or in those aspects where the particle includes a target molecule that facilitates uptake, receptor-mediated endocytosis.

The cell may be a phagocytic cell. Examples of phagocytic cells include, but are not limited to, macrophages, monocytes, monocyte-derived macrophages, granulocytes, and neutrophils. Other examples of cells include those that are non-phagocytic or weakly phagocytic, such as lymphocytes (including T-lymphocytes and B-lymphocytes), natural killer cells, red blood cells, muscle cells, bone marrow cells, stem cells, bone cells, vascular cells, organ tissue cells, neuronal cells, basophils, eosinophils, dendritic cells, and endothelial cells. The cells may be mammalian cells, such as primate (e.g., human or monkey), or murine (e.g., rat or mouse).

The methods disclosed herein may be used with cells that are in vitro, ex vivo, or in vivo. In vitro refers to cells present in cell culture and capable of long term culture in tissue culture medium. Ex vivo refers to cells that have been removed from the body of a subject and are capable of limited survival in tissue culture medium. In vivo refers to cells that are present within the body of a subject. Examples of useful in vitro cells include, but are not limited to, CES cells, human peripheral blood mononuclear cells, and human T-cells. Useful ex vivo cells may be obtained commercially (e.g., All-Cells, LLC, Emeryville, Calif.) or using cell separation devices. Various cell types may be enriched from biological samples using routine methods known in the art. For instance, bone marrow cells and monocytes may be enriched from bone marrow and peripheral blood, respectively. Cell culture conditions for maintaining cells in vitro and ex vivo are known and used routinely by those skilled in the art.

When contacting cells in vitro or ex vivo, a composition described herein may be mixed with the cells under conditions suitable for uptake of the particles. Suitable conditions may include a temperature of between 35° C. and 39° C., preferably 37° C., and use standard cell culture conditions. Typically, the cells and the composition are incubated together for a period of time sufficient for uptake of particles by the cells, for instance, between 30 minutes and 90 minutes. Ex vivo cells contacted with a composition described herein may be implanted into the subject from which they were explanted, or into another subject.

In some aspects a cell may include a pathogenic microbe, such as bacteria, viruses, fungi, and parasites. Examples of viruses include retroviruses, such as HIV-1, HIV-2, simian immunodeficiency virus (SIV), and feline immunodeficiency virus (FIV).

The methods may be directed to treating one or more signs of certain conditions in a subject, such as a primate (e.g., human or monkey) or murine animal (e.g., rat or mouse). In this aspect the method may include administering an effective amount of a composition described herein to a subject having or at risk of having a condition, or signs of a condition. Optionally, the method may further include determining whether at least one sign of the condition is changed, preferably, reduced.

In those aspects directed to contacting an in vitro cell or an ex vivo cell with a composition described herein, an "effective amount" of a composition is an amount effective to result in an intracellular concentration of each agent present in the particles. The intracellular concentration may be at least the $IC_{50}$ of each agent, or at least the $IC_{90}$ of each agent. Typically, the level of each agent present in the cells is independent. In those aspects directed to administering a composition in vivo or contacting an ex vivo cell with a composition described herein and subsequently reimplanting the ex vivo cells into a subject, an "effective amount" of a composition is an amount effective to result in a concentration of each agent in serum of at least the $IC_{50}$ or at least the $IC_{90}$. The concentration of each agent may be expressed as nanogram (ng)/milliliter (ml) or nano-moles (nM)/ml. The serum concentration of each agent may be least 100 ng/ml, and no greater than 500 µg/ml, no greater than 1000 ng/ml, or no greater than 500 ng/ml. Typically, the serum concentration of each agent is elevated for at least 21 days, at least 25 days, or at least 30 days after a single administration. The tissue concentration of each agent may be at least 0.1 µg/gram tissue, at least 0.5 µg/gram tissue, at least 1 µg/gram tissue, at least 5 µg/gram tissue, or at least 10 µg/gram tissue, and no greater than 500 µg/gram tissue, or no greater than 100 µg/gram tissue. Typically, the tissue concentration of each agent is elevated for at least 15 days, at least 21 days, or at least 25 days after a single administration. Administration of a composition in vivo or contacting an ex vivo cell with a composition described herein and subsequently reimplanting the ex vivo cells into a subject can prevent the manifestation of signs of a disease, decrease the severity of the signs of a disease, and/or completely remove the signs.

The conditions may be caused by an infection or an inflammatory disease. As used herein, the term "infection" refers to the presence of and multiplication of a pathogenic microbe in the body of a subject. The pathogenic microbe may be intracellular or extracellular. The infection can be clinically inapparent, or result in symptoms associated with disease caused by the microbe. The infection can be at an early stage, or at a late stage. Examples of pathogenic microbes include bacteria, viruses, fungi, and parasites. Examples of viruses include retroviruses, such as HIV family of retroviruses (for instance, HIV-1, HIV-2, SIV, or FIV. Examples of conditions caused by the HIV family of retroviruses include AIDS-related conditions, such as AIDS, AIDS-related conditions including AIDS-related complex (ARC), progressive generalized lymphadenopathy (PGL), anti-HIV antibody positive conditions, and HIV-positive conditions, AIDS-related neurological conditions (such as dementia or tropical paraparesis), Kaposi's sarcoma, thrombocytopenia purpurea and associated opportunistic infections such as *Pneumocystis jirovecii* pneumonia, Mycobacterial *tuberculosis*, esophageal candidiasis, toxoplasmosis of the brain, CMV retinitis, HIV-associated dementia (HAD), HIV-related encephalopathy, and HIV-related wasting syndrome.

Treatment of signs associated with these conditions can be prophylactic or, alternatively, can be initiated after the development of a condition described herein. As used herein, the tetra "sign" refers to objective evidence in a subject of a condition. Signs associated with conditions referred to herein and the evaluations of such signs are routine and known in the art. Treatment that is prophylactic, for instance, initiated before a subject manifests signs of a condition, is referred to herein as treatment of a subject that is "at risk" of developing the condition. Typically, a subject "at risk" of developing a condition is a subject present in an area where subjects having the condition have been diagnosed and/or is likely to be exposed to an agent, such as a microbe, causing the condition. Accordingly, administration of a composition can be performed before, during, or after the occurrence of the conditions described herein. Treatment initiated after the development of a condition may result in decreasing the severity of the signs of one of the conditions, or completely removing the signs.

In those aspects where the subject is being treated for HIV infection, methods for measuring in vivo HIV infection and progression to AIDS are known to the skilled person and can be used to determine whether a subject is responding to treatment. For example, a subject's $CD4^+$ T cell count can be monitored. A rise in $CD4^+$ T cells indicates that the subject is benefiting from administration of a particle described herein.

The present invention is illustrated by the following examples. It is to be understood that the particular examples, materials, amounts, and procedures are to be interpreted broadly in accordance with the scope and spirit of the invention as set forth herein.

EXAMPLE 1

Combination antiretroviral therapy (ART) continues to be the mainstay for HIV treatment. HIV-1 hidden in bodily sanctuaries, such as brain and testes, leads to an inaccessability of adequate drugs to these areas. Nanoparticles may be a drug delivery option to deliver ART into these sanctuaries. Poly-(lactic-co-glycolic acid) (PLGA) nanoparticles (NPs) containing ritonavir (RTV), lopinavir (LPV), and efavirenz (EFV) were fabricated using multiple emulsion-solvent evaporation procedure. The nanoparticles were characterized by electron microscopy and zeta potential and the in vitro release of antiretroviral therapy from the nanoparticles incubated with peripheral blood mononuclear cells (PBMCs) over 28 days was evaluated. Nanoparticles size was 262+53.9 nm and zeta potential was −30+12.4. ART loading averaged 7% (w/v). ART (100 µg of each drug in nanoparticles) levels were determined in PBMCs after culture. Intracellular peak antiretroviral therapy levels from nanoparticles (day 4) were RTV 2.5+1.1; LPV 4.1+2.0; and EFV 10.6+2.7 µg. Detectable intracellular ART levels at day 28 were >0.9 µg/mL. Free drug (25 µg of each drug) dissolved in ethanol and added to PBMCs served as control was eliminated within 2 days. Cellular MTT assay demonstrated that nanoparticles are phagocytized by human macrophages and are not significantly cytotoxic. These results demonstrated antiretroviral therapy nanoparticles can be fabricated containing three antiretroviral drugs (RTV, LPV, EFV). Sustained release of antiretroviral therapy from PLGA nanoparticles show high drug levels at day 28. PLGA nanoparticles do not produce significant cytotoxicity.

Methods

Nanoparticle (NP) preparation: ART (ritonavir, lopinavir, efavirenz; one mg of each) were prepared using a water-in-oil-in-water homogenization. Briefly, in a typical procedure, a solution of ethylene oxide/propylene oxide block copolymer (Poloxamer-127; 2% [w/v] in double distilled water (ddH2O 10 mL); BASF, Mt. Olive, N.J.) was homogenized with ART drug powder (1 mg of each) in poly-lactic-co-glycolic acid) (PLGA) polymer (molecular weight 110,000-139,000 Daltons (100 mg) in 10 mL methylene chloride) using a probe sonicator (21W for 6 min) (Sonicator XL, Misonix, Farmingdale, N.Y.). The water-in-oil emulsion thus formed was further emulsified into 30 mL of 0.25% (w/v) aqueous solution of polyvinyl alcohol (PVA) as an emulsifier by using sonication as described above for 5 minutes to fowl multiple water-in-oil-in-water emulsion. NPs containing osmium tetroxide, an electron-dense agent, were formulated similarly, except that 10 mg of osmium tetroxide, and one milligram of each ART was added to the polymer solution. Additionally, 6-hydroxycoumarin (a fluorescent dye; 1% w/v) was added to the polymer solution and one milligram of each ART were fabricated to make fluorescent nanoparticles for flow cytometry. In all formulation procedures, the emulsion was stirred for approximately 18 hours at room temperature to evaporate the organic solvent, methylene chloride, followed by ultracentrifugation (15,000 G for 45 minutes at 4° C., Optima LE-80K, Beckman, Palo Alto, Calif.), rinsed twice with ddH2O to remove PVA, and unentrapped drugs, and then lyophilized (Labconco, Freezone 4.5 at −52° C. and 5.62 torr) for 24 hours to obtain a dry powder.

Nanoparticle characterization: Nanoparticles were evaluated for size by zeta potential as well as scanning electron microscopy (SEM) and surface charge by using a zeta potential analyzer (ZetaPlus, Brookhaven Instruments, Holtsville, N.Y.). For SEM, a sample of nanoparticles was suspended in water (0.2 mg/ml) and an aliquot of suspended particles were placed onto a tip and sputter coated with 2% w/v uranyl acetate, dried, and then visualized by using a JEOL-40A (JEOL Ltd, Sheboygan, Wis.) scanning electron microscope. Additionally, one milligram of formed particles was dissolved in one milliliter methylene chloride in glass tubes and evaporated overnight in quadruplicate. High pressure liquid chromatography (HPLC) mobile phase (200 µL) reconstituted the tubes. The tubes were centrifuged (11,000 rpm, 10 minutes, 4° C.) and aliquots were injected into the HPLC equipment to determine ART drug loading and entrapment efficiency.

High pressure liquid chromatography (HPLC): HPLC was performed using a previously reported method (Weller et al., J. Chromatogr. B Analyt. Technol. Biomed. Life Sci., 2007, 848(2):369-73). Briefly, the equipment included a pump (LC-10ATvp), system controller (SIL-10ADvp); degasser unit (DGU-14A), refrigerated auto-sampler (SIL-10ADvp); and a UV-Vis detector (SPD-10ADvp) and a column heater (set at 35° C.) (all from Shimadzu Corporation, Columbia, Md.). Samples were run through a C18 pre-column and a Jupiter C18 reverse-phase [150×3.9 mm (I.D.)] with 5 mm particle size packing (Phenomenex, Torrance, Calif.). The mobile phase was 25 mM KHPO4 (pH 4.9) and acetonitrile (40:60). The mobile phase was filtered and degassed prior to use. Flow rate was set at 0.9 mL/min and the detector was set at 212 nm. Samples of know amounts of the ART drugs (lopinavir, ritonavir, and efavirenz) were diluted to obtain a 30-510 ng/ml standard curve. Peak area from the samples and standards were integrated using EZ-Start chromatography software (Shimadzu) on a Dell computer. Injection volume was 20 µL and all samples were analyzed in duplicate and averaged. Standards were analyzed in triplicate and averaged. Inter-day and intra-day variability was always <10%.

Human monocyte isolation and cultivation: Human PBMCs were obtained from whole blood collection of HIV-1, -2 and hepatitis B seronegative donor and purified using CPT Vacutainer tubes (BD and Co., Sparks, Md.) according to the manufacturer instructions. Polymorphonuclear cells ($1\times10^6$ cells/mL) were cultured in DMEM supplemented with 10% heat-inactivated pooled human serum, 1% glutamine, 1% penicillin-streptomycin, and 10 g/mL ciprofloxacin (Sigma Chemical Co) then filter sterilized. The PBMCs were used within 2 hours after blood collection. Media was one-half exchanged with fresh media every 2-3 days. These cells were used for ART drug release experiments from nanoparticles as determined by HPLC. Human PBMCs at $5\times10^6$ were cultured in DMEM supplemented with 10% heat-inactivated pooled human serum, 1% glutamine, 1% penicillin-streptomycin, and 10 g/mL ciprofloxacin (Sigma Chemical Co), and 1000 U/mL highly purified recombinant human macrophage colony stimulating factor (MCSF; R&D Systems, Inc; Minneapolis, Minn.) for seven days. Media was one-half exchanged very 2-3 days. Monocyte-derived macrophages (MDM) were used for TEM and fluorescent imaging.

ART Release from Nanoparticles: Antiretroviral nanoparticles (100 µg) were added to PBMC cell cultures. Flasks containing PBMCs and ART nanoparticles were placed in a 37° C., 5% $CO_2$ incubator. At the appointed time, media in the flask was placed in a sterile 15 mL conical tube and centrifuged (400×G, 24° C. for 10 minutes). Cells (250 µL) were removed from the tube and put into a microfuge tube for HPLC analysis. Cell samples were obtained every 2 hours for the first 8 hours, then 2, 4, 10, 14, 21, and 28 days. Cell samples were placed in microfuge tubes, 250 µL of 100% methanol was added to lyse the cells then the cells were frozen (−20° C.) until assayed for ART drugs using HPLC. When HPLC was performed, microfuge tubes were thawed, centrifuged at 15,000 rpm at 4 C for 10 minutes and an aliquot of supernatant was placed into autosampler vials with glass insert. Free drugs (25 µg/mL of each ART drug) was dissolved in HPLC-grade ethanol, incubated with the PBMCs and cells were removed at 2, 4, 8, 24, and 48 hours, lysed with methanol, centrifuged, and assayed by HPLC as controls of these experiments.

Electron microscopy: To determine the shape and size of ARV nanoparticles, nanosuspensions were examined with a JEOL 40A scanning electron microscope. NP shape and structural integrity were examined in thin sections. For TEM, monocyte-derived macrophages were exposed to ART nanoparticles at $5\times10^{-6}$ M for 30 minutes and 1 hour. Cells were rinsed with PBS, fixed with 2.5% glutaraldehyde for 24 hours, post-fixed with 1% osmic acid, dehydrated in graded ethanol solutions, and embedded in Epon 812 mixture. Thin sections were cut and stained with 2% uranyl acetate and examined under a JEOL-1011.

Analysis of fluorescent ART nanoparticle uptake: The ability of monocyte-derived macrophages to uptake fluorescent ART nanoparticles was assessed using FLOW cytometry analysis and direct immunofluorescence microscopy. Monocyte-derived macrophages at $5\times10^5$ monocyte-derived macrophage were incubated in the presence of fluorescent ART nanoparticles for 30 and 60 minutes. Monocyte-derived macrophages cultured in the absence of nanoparticles were used as controls. For FLOW cytometry analysis, control and monocyte-derived macrophages incubated with fluorescent ART nanoparticles were scraped from 6 well culture plates following incubation, centrifuged for 2-4 minutes at 1,200 rpm, rinsed in phosphate buffered saline (PBS), and fixed in 10% buffered formalin. Fixed cells were resuspended and samples were run on a UV SORP FACSAria (BD Biosciences, San Jose, Calif.). FLOW used 100 mW Coherent Saphire laser set at 488 nm for excitation and was detected using a 530/30 bandpass filter (looking at light between 515 nm and 545 nm). For immunofluorescence microscopy, 2.5×10$^5$ monocyte-derived macrophages were plated onto tissue culture treated glass coverslips and incubated with fluorescent ART nanoparticles for 30 and 60 min. Control monocyte-derived macrophages were cultured without nanoparticles. Following incubation, cultured monocyte-derived macrophages were rinsed with PBS and fixed in 4% paraformaldehyde in PBS. Cells were visualized with an inverted fluorescent microscope (DMI4000B, Leica) and images were acquired using Image ProPlus software (Media Cybernetics; Bethesda, Md.).

Analysis of macrophage viability: Monocyte-derived macrophage viability following exposure to and phagocytosis of nanoparticles was measured by using the MTT (3-(4,5-dimethylthiazol-2-yl)-2,5-diphenyltetrazolium bromide) method (Denizot et al., J Immunol Methods, 1986, 89:271-277). Active mitochondrial dehydrogenases in healthy cells convert MTT generating water-insoluble, purple formazan crystals that are measured by spectrophotometric techniques (Hansen et al., J. Immunol. Methods, 1989, 119:203-210). For each MTT assay, 2.5×10$^5$ differentiated human macrophages were plated on 24 well tissue culture plates in culture media overnight at 37° C. and 5% $CO_2$. Macrophages were incubated with or without ART nanoparticles immediately preceding and one hour prior to application of MTT. Macrophages were allowed to metabolize MTT (5 mg/ml in DMEM supplemented media) for 30 or 60 min at 37° C. and 5% $CO_2$. Media was removed from cultured macrophages and cells were treated with 100% dimethyl sulfoxide to lyse the cells and dissolve formazan crystals. Lysates were transferred to 96 well plates for analysis. Absorbance of the lysate was measured at 595 nm using a precision microplate reader (Molecular Devices, model S/NE10984). Blank wells were subtracted as background from each triplicate sample and the samples were averaged.

Results

ART size and particle charge were measured (n=9) and average values (+SEM) were 262+53.9 and −30+12.4, respectively. FIG. 1 depicts the SEM photomicrograph of ART nanoparticles. ART drugs were analyzed by HPLC for nanoparticle loading and loading efficiency. Antiretroviral drug loading averaged 4.9%, 5.2%, 10.8% for RTV, LPV, and EFV, respectively. Entrapment efficiency averaged 38%, 45%, and 86% for RTV, LPV, and EFV, respectively.

Figure 2:
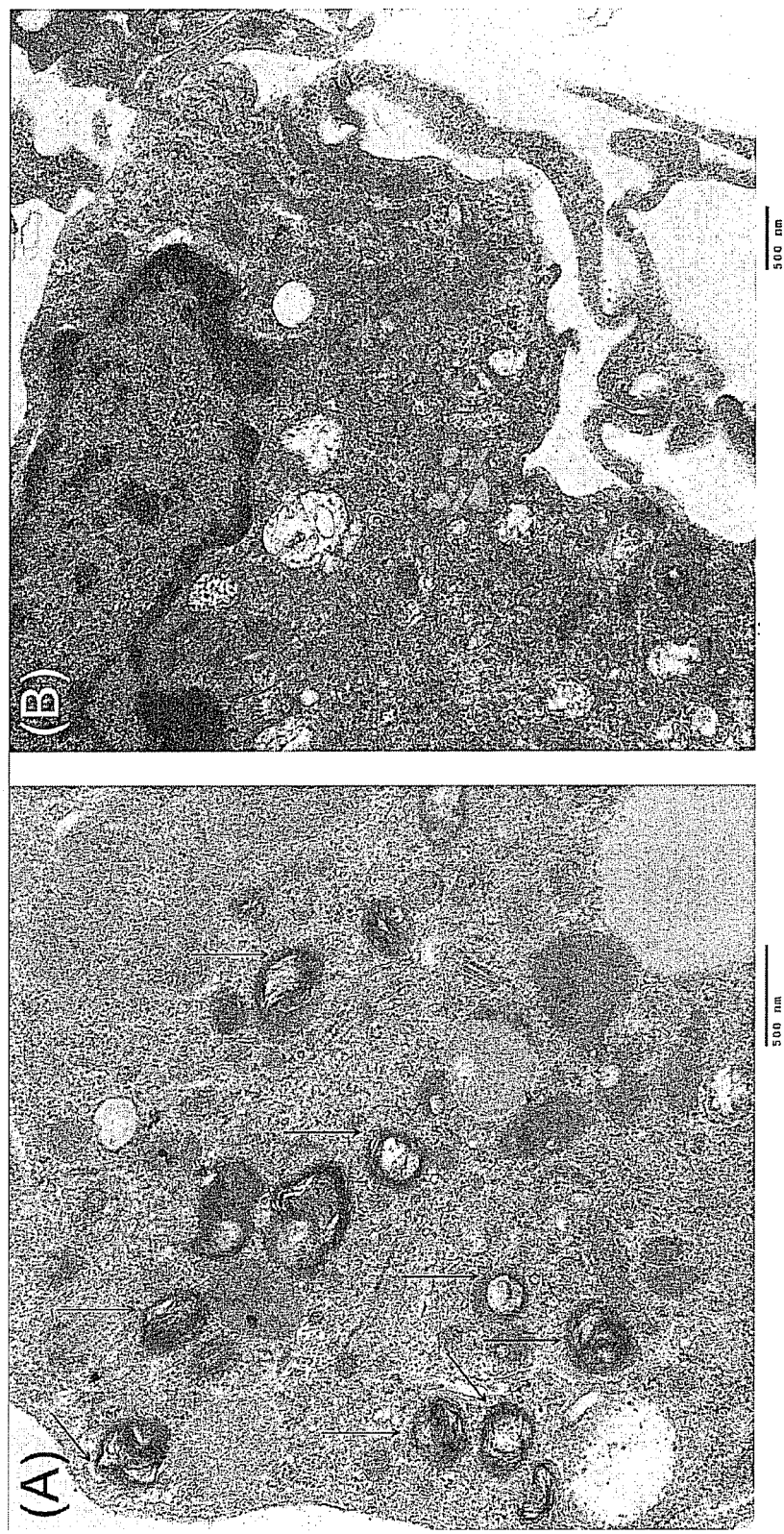
FIG. 2. Transmission electron microscopy (TEM) of nanoparticles in monocyte-derived macrophages. Transmission electron microscopy (TEM) of nanoparticles within macrophages. Photos are high magnification of monocyte-derived macrophages containing antiretroviral nanoparticles (arrows; A) and control monocyte-derived macrophages (B) ladened with osmium tetroxide after 45 minutes of incubation (Mag×40,000).

Osmium tetroxide ladened ART nanoparticles were incubated with macrophages for 0, 0.5, and 1 hour. FIG. 2 show TEM photomicrographs of osmium tetroxide ladened ART nanoparticles within macrophages as well as ART nanoparticles undergoing phagocytosis.

Figure 3:
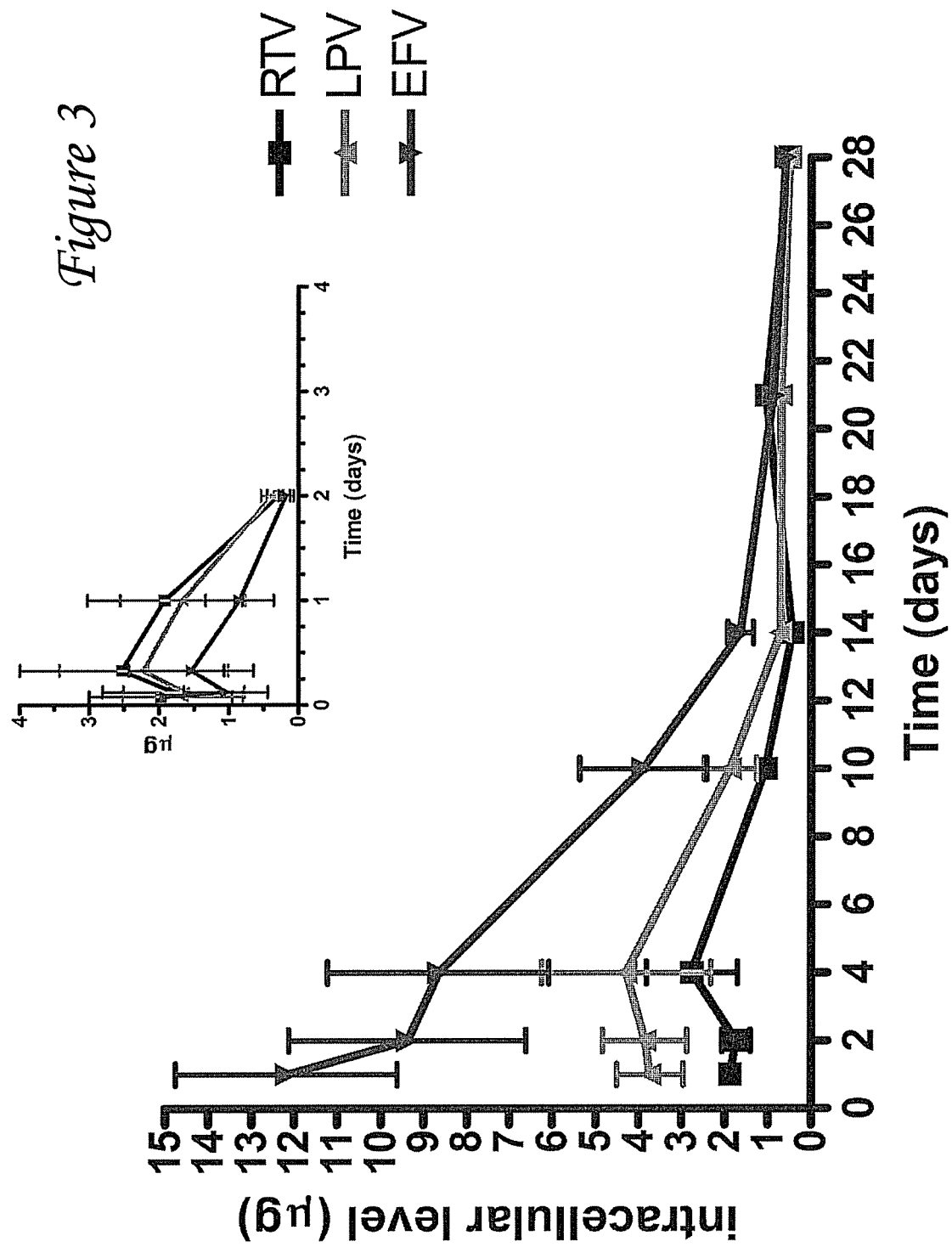
FIG. 3. In vitro antiretroviral therapy release from nanoparticles incubated in polymorphonuclear cells. Intracellular ritonavir, lopinavir, and efavirenz levels in polymorphonuclear cells over time. The insert figure is the intracellular free drug levels in polymorphonuclear cells over time.

Antiretroviral drug release from PLGA nanoparticles incubated with polymorphonuclear cells (PBMCs) is shown in FIG. 3. The inset figure is the HPLC analysis of the free drug incubated with the PBMCs. Free drug incubated with PBMCs demonstrate removal of ART drugs by day 2 in vitro. When the cells were lysed and analyzed by HPLC, the intracellular concentrations of the three drugs peaked at 8 hours (RTV 5.1+0.05; LPV 4.3+0.03; and EFV 3.1+0.02 µg) and were eliminated by 48 hours. In contrast, when ART were fabricated into a NP and incubated in PBMCs, intracellular ART peak concentrations were at 96 hours (RTV 2.5+1.1; LPV 4.1+2.0 µg). Efavirenz intracellular concentration peaked at 24 hours (10.6+2.7 µg). All three drugs continued to be released for 28 days. The 28 day concentrations for the three ARTs were >0.9 µg.

Figure 4:
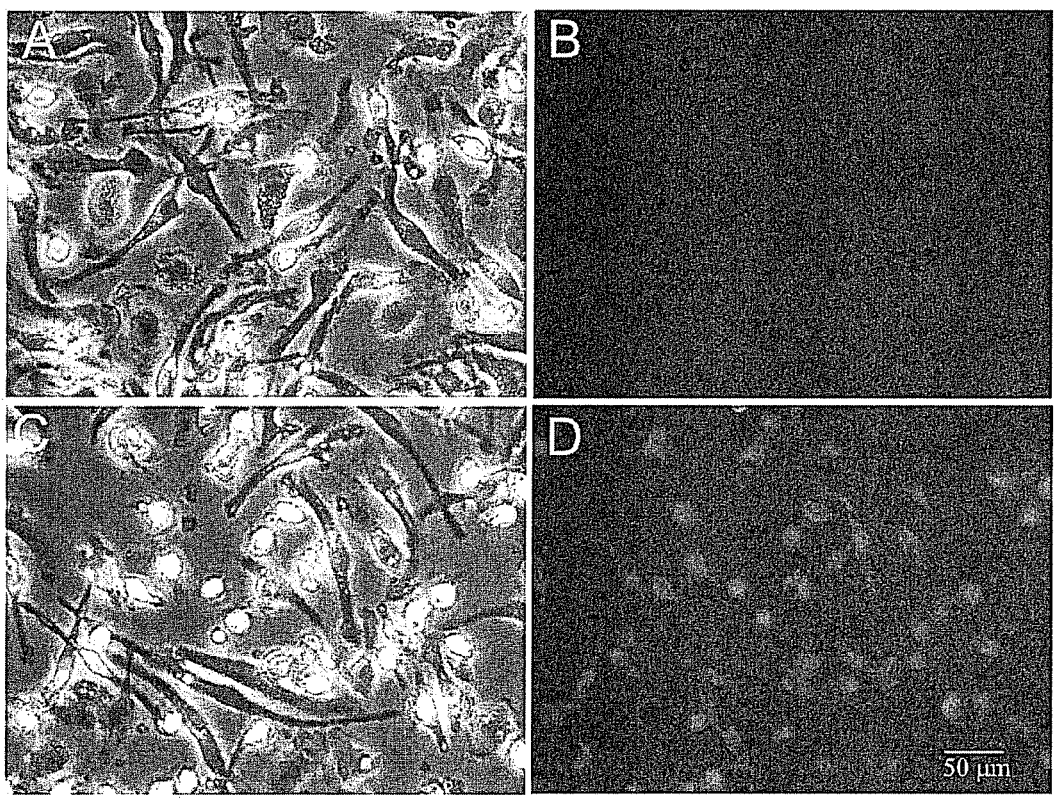
FIG. 4. Fluorescent nanoparticle uptake by human monocyte-derived macrophages. A and B are control phase and fluorescent photomicrographs of human monocyte-derived macrophages in the absence of fluorescent NPs. Following 30 min incubation with NPs, monocyte-derived macrophages fluoresce due to NP uptake (C and D; 40X objective).

6-Hydroxycoumarin (fluorescent dye) was used to determine the efficiency with which macrophages phagocytize fluorescent nanoparticles. Fluorescent macrophages were observed by FLOW cytometry as well as by fluorescent microscopy. FLOW cytometry data shows that virtually all macrophages phagocytized fluorescent nanoparticles. Direct fluorescence showed the presence and relative localization of nanoparticles in macrophages following incubation and uptake (FIG. 4). While all imaged cells show uptake of the fluorescent ART nanoparticles, fluorescence is not seen in control cells.

Figure 5:
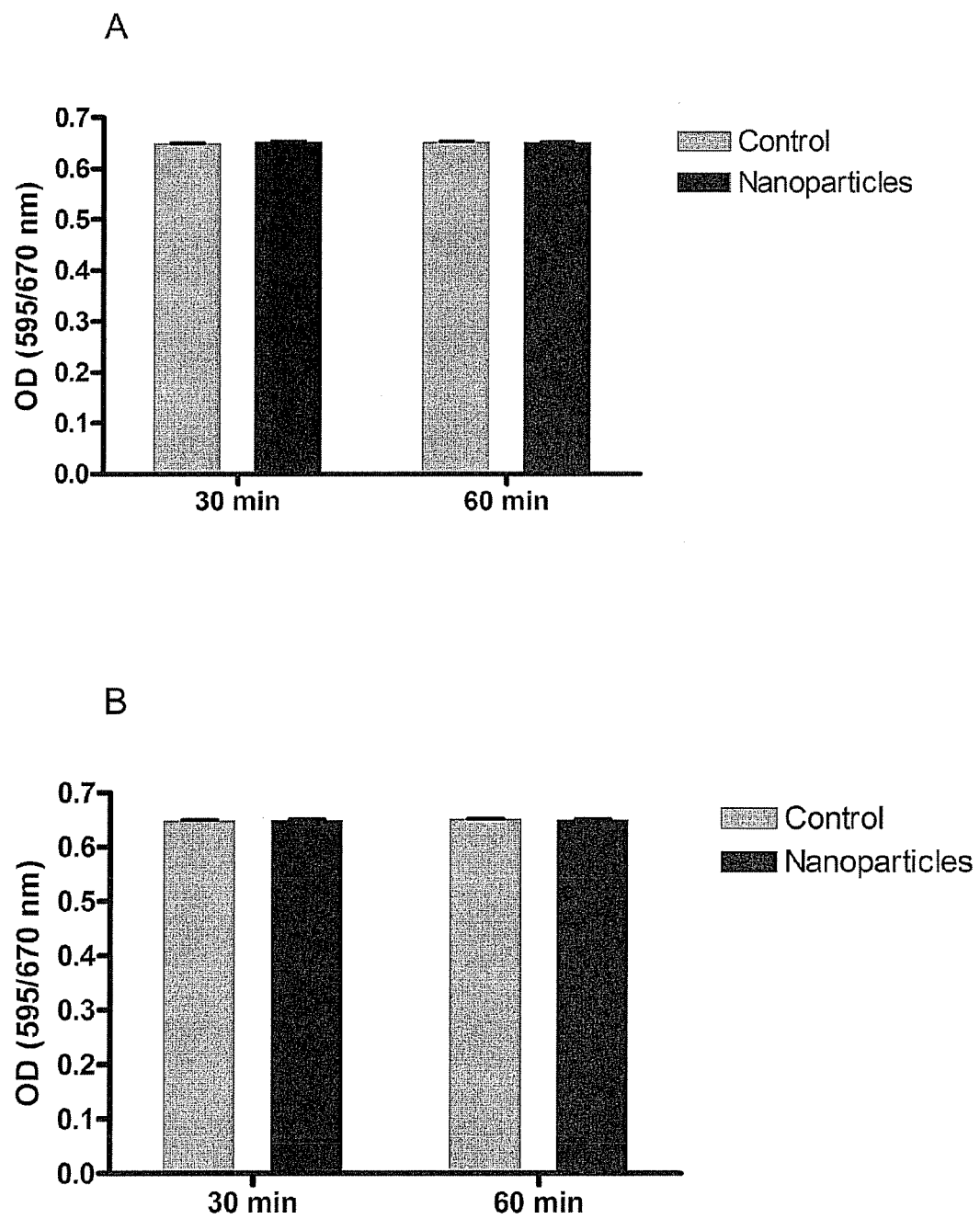
FIG. 5. MTT assay results. Graphical representation of MTT assay for control macrophages (monocyte-derived macrophages) and monocyte-derived macrophages incubated with nanoparticles. Nanoparticles and MTT substrate were immediately added to the media of cultured human monocyte-derived macrophages MTT assays were performed after 30 and 60 minutes (Panel A) of incubation. Alternatively, monocyte-derived macrophages were incubated with and without nanoparticles for 1 hour before the MTT substrate was added and an MTT assay was performed after 30 and 60 minutes (Panel B) of incubation.

To address whether the uptake of ART nanoparticles by macrophages affected cell viability, MTT assays were performed (FIG. 5). MTT assays measure the viability of cells by assessing the presence of active mitochondrial dehydrogenases that convert MTT into water-insoluble, purple formazan crystals. Solubilization and analysis of formazan conversion demonstrates that immediately following nanoparticle addition and one hour after nanoparticle uptake the viability of macrophages is not significantly different from control conditions. Taken together these cellular assays demonstrate that ART nanoparticles are phagocytized by macrophages and uptake of ART nanoparticles does not interfere with macrophage viability.

Discussion

The use of nanotechnology has exploded in the recent years. Nanoparticles were initially developed as carriers for vaccines and cancer chemotherapy agents (Couvreur et al., J. Pharm. Sci., 1982, 71:790-792, Beck et al., J. Microencapsul., 1993, 10:101-114, Conway et al., Vaccine 2001, 19:1940-1950). The use of nanotechnology as a drug delivery system has mainly been investigated for the treatment of malignancies. Nanoparticles can concentrate preferentially in tumor masses, inflammatory sites, and infectious sites by utilization of enhanced permeability and retention (ERP) effect on the vasculature (Shenoy et al., Pharm. Res., 2005, 22:2107-2114). Modifying oncologic drugs into nanoparticles and delivering the drug to the malignant tissue has resulted in significant preliminary results in animal models (Sengupta et al., Nature, 2005, 436:568-572). Indeed, this is where the majority of research has been focused (Brannon-Pepas et al., Adv. Drug Del. Rev., 2004, 56:1649-1659).

Other investigators have been able to fabricate single antiretroviral drugs into a nanoparticle delivery system (Dou et al., Blood, 2006, 108:2827-2835, Dou et al., Virology, 2007, 358:148-158, Gorantla et al., J. Leukoc. Biol., 2006, 80:1165-1174, Gagne et al., Biochem. Biophy. Acta, 2002, 1558:198-210, Bender et al., Antimicrob Agents Chemother., 1996, 40:1467-1471, Kuo et al., Ent J. Pharmaceut., 2005, 290:161-172, Shah et al., Pharm Res., 2006, 23:2638-2645). However, the use of a single antiretroviral drug in the treatment of HIV-1 only results in development of resistant strains and treatment failures. Combination drugs are currently the standard of practice for HIV-1 therapeutics. Our results demonstrate that three drugs can be incorporated into a single nanoparticle for drug delivery.

The results of cellular assays show that macrophages engulf these particles. This is advantageous as HIV-1 requires host DNA replication for survival. Providing a means to get significant drug concentrations intracellularly would inhibit the replication of HIV-1 in the reticular endothelial system (RES) where macrophages migrate. Further studies are ongoing to determine this. Additionally, MTT assay results show that PLGA particles do not produce significant cellular toxicity. This is also advantageous for development of these nanoparticles as a drug delivery modality for human use. Taken together, our data show that these inert particles are taken up by the macrophages and have a sustained-release profile.

Viral reservoirs within the body have prevented total eradication of HIV-1 with successful ART (Chun et al., Nature 1999, 401:874-875). A number of studies have demonstrated persistent, low level HIV-1 replication in patients receiving oral highly active antiretroviral therapy (HAART) that renders them aviremic (Zhang et al., N. Engl. J. Med., 1999, 340:1605-1613, Natarajan et al., Lancet, 1999, 353:119-120, Ramratnam et al., J. Acquire Immune Defic. Syndr., 2004, 35:33-37). These studies provide evidence that continued viral replication occurs in lymphoid reservoirs. Our studies show PLGA ART nanoparticles within the cytoplasm of macrophages. The PLGA ART nanoparticles are phagocytosized by macrophages and these could deliver high ART levels to lymphoid reservoirs and could positively affect persistent, low level viral replication. This could prevent the development of mutant HIV-1 virions to ART drugs. Further research is necessary to determine the concentration of ART drugs in these lymphoid reservoirs as well as gut-associated lymphoid tissue (GALT) (Chun et al., J. Infect. Dis., 2008, 197:714-720).

The results of these experiments demonstrate for the first time that combination antiretroviral drugs can be loaded efficiently into a nanoparticle drug delivery system. Our data show that sustained drug release over the course of 28 days is possible. The goal of drug delivery systems is cellular uptake and release with no cytotoxicity. Indeed, this drug delivery system is advantageous as it could preclude the need for daily administration of oral drugs to maintain active concentrations in HIV-1 tissues with lower total amount of drug exposure. Therefore, this delivery method may be useful for patients that are nonadherent to orally administered HAART and may offer other patients treatment options. If patients received ~100% of their ART drugs, the development of resistance would slow and the efficacy and durability of ART drug therapeutics would be enhanced (Palepu et al., Drug Alcohol Depend., 2006, 84:188-194, Farmer et al., Bulletin World Health Org., 2001, 79:1145-1151, Rockstron et al., AIDS Res. Hum. Retroviruses, 2008, 2:141-148). Of note, an investigational non-nucleotide reverse transcriptase inhibitor (NNRTI) capable of once every 8 weeks administration was recently presented showing that sustained delivery of antiretrovirals may be utilitzed clinically (G. Van t'Klooster, R. Verloes, L. Baert, et al. Fifteenth Conference on Retroviruses and Opportunistic Infections, Boston. Abstract 134, 2008.) Further studies are necessary to produce reliable data regarding the pharmacology and efficacy of this delivery system. These data provides further evidence that sustained release of multiple ART drugs from a nanoparticle drug delivery system present a viable option for treatment of HIV-1.

Conclusions

The results of these experiments demonstrate that PLGA polymer can be used to fabricate nanoparticles for combination ART to develop a drug delivery system that can be used for lymphoid tissue HIV-1 reservoir treatment. Furthermore, this delivery system has prolonged release of combination ART for 21 days. The particles penetrate macrophages and do not cause toxicity to these cells by MTT assay. Further study is necessary to determine optimization of ART drug combinations as well as drug concentrations in lymphoid tissue. This could be a promising new delivery system for the management of HIV-1 infected patients.

EXAMPLE 2

Pharmacokinetics of Antiretroviral Release from PLGA Nanoparticles in Mice

Combination antiretroviral drugs (RTV, LPV, EFV) were fabricated into poly (DL-lactide-co-glycolide) (PLGA) nanoparticles (NPs) for sustained delivery. A comparison of free drugs (500 μg each) to antiretroviral (AR) NPs time course in mice is presented here. PLGA NP containing RTV, LPV, and EFV were fabricated using a water-in-oil-in-water multiple emulsion. The particles were weighed, reconstituted with PBS and 500 μg was injected intraperitoneally (IP) into male BALB/c mice. At specific times, (free: 0.08, 0.167, 0.25, 0.33, 1, 2 and 3 days; antiretroviral nanoparticles: 0.167, 0.33, 1, 2, 4, 7, 14, 21, 28, and 35 days) mice (n=3/time point) were euthanized and selected organs and serum were harvested for antiretroviral drug levels. Results are presented as mean±SEM. Peak antiretroviral drug levels in the serum were found to be at 4 hours post-injection (RTV 3.2±1.5, LPV 3.3±1.6, EFV 3.5±1.9 μg/L). Serum elimination half-lives were approximately 11.6 hrs for all AR. Free drugs were eliminated by day 3 in all tissue except brain. Animals injected with PLGA NP had detectable RTV, LPV, and EFV levels in all tissues excised from animals up to day 28 post-injection. The highest AR levels at day 28 were in the liver (RTV 0.473±0.057; LPV 1.2±0.19; EFV 1.02±0.44 μg/G). These results demonstrate that PLGA NPs have sustained release properties up to 28 days after injection in vivo. PLGA NPs containing RTV, LPV, and EFV could be a treatment modality for the sustained delivery of antiretroviral drugs.

Methods:

Antiretroviral nanoparticles containing ritonavir, lopinavir, and efavirenz were fabricated using homogenization as described in Example 1. Briefly, a water-in-oil-in-water emulsion of poly (DL-lactide-co-glycolide) polymer in methylene chloride containing 20 mg of each of the antiretroviral drug powders (Sequoia Research Products, Ltd., Great Britain) was prepared. This was homogenized in 0.2% poly vinyl alcohol and then added to 2% Pluronic F-127 at 100W. The emulsion was allowed to evaporate the methylene chloride, twice washed with double-distilled water, centrifuged at 15,000 RPM for 30 minutes each, freeze-dried for 24-48 hours. Drug loading and entrapment efficiency were determined as described in Example 1.

The nanoparticle powder was weighed and 500 μg was dissolved in phosphate-buffered saline (PBS) and injected intraperitoneally into each BALB/c male mice (25-28 g). Free drug powder (500 μg) of ritonavir, lopinavir, and efavirenz was dissolved in 25 μL/mouse of ethyl alcohol and then further dissolved in PBS and injected intraperitoneally. At specified times points, mice (n=3-4) were euthanized using a $CO_2$ chamber and organs (spleen, liver, kidney, brain, testes) and blood (100-150 μL) were removed from each of the mice. Blood was allowed to clot, centrifuged (1000×G) and serum was harvested. The organs were harvested and immediately placed on ice. At weekly intervals, an aliquot of the organ tissue was weighed and 500 μL of 100% methanol was added to tissue and serum samples. The tissue was homogenized using a pellet homogenizer, equilibrated at 4° C. for 30 minutes, and then centrifuged (11,400 RPM×15 minutes at 4° C.). An aliquot of the supernatant (20 μL/injection) was added to autosampler vials with glass inserts. The high pressure liquid chromatography (HPLC) instrument (Shimadzu, Corp, Columbia, Md.) used a previously published HPLC method to determine lopinavir, ritonavir, and efavirenz concentrations (Weller et al., J. Chromatogr. B Analyt. Technol. Biomed. Life Sci., 2007, 848(2):369-73). Duplicate samples from tissues and serum were assayed and standards were assayed in triplicate. The organ/serum samples were compared to the standard curve (45-1000 ng/ml) that was performed on that day using peak area and EZ-Chrom software (Shimadzu, Corp.).

Monocytes were purchased (AllCells, LLC, Emeryville, Calif.) and shipped frozen. Once received, the cells ($1\times10^6$/ml) were thawed at 37° C. in a water bath and placed in DMEM media containing 1% L-glutamine, 1% penicillin-streptomycin, and 50 µg/ml ciprofloxacin and filtered sterilized and then 1000 U/ml M-CSF was added (R & D Systems, Inc. Minneapolis, Minn.) to differentiate into macrophages. Media was half-exchanged every 2-3 days for a total of 7 days. Monocyte-derived macrophages (MDM) were infected with HIV-$1_{ada}$ (AIDS Research Resources, NIH, Bethesda, Md.) and one-half media was collected for up to 20 days starting on day 6, filtered through a 0.22 u filter and frozen for p-24 ELISA determination. MDMs ($1\times10^6$) were also added to 96 well plates and differentiated using media containing M-CSF. Triplicate columns of the 96-well plates were used to determine tissue culture infective dose ($TCID_{50}$), triplicate columns were used to determine free drug $IC_{50}$, and triplicate columns were used to determine nanoparticle $IC_{50}$. This was performed on several days of collected virus (days 8, 11, and 13). Media supernatant was withdrawn from the 96 well plates and analyzed for p-24 using a monoclonal sandwich ELISA according to the manufacturer's instructions. The p-24 ELISA was used to determine the in vitro inhibition of HIV (MOI 0.01) by the free drugs and NPs.

Data is presented as mean±SEM where appropriate. Serum concentration-time curves were used to determine pharmacokinetic parameters. Elimination rate constant was determined using nonlinear regression of the terminal phase of the serum concentration-time curve. Apparent volume of distribution, total body clearance, mean residence time and area under the serum concentration-time curve to the last concentration obtained ($AUC_{0-last}$) were determined by non-compartmental modeling. Peak lopinavir, ritonavir, and efavirenz levels and time for peak levels were determined by examination of the serum concentration-time curves.

Results

Figure 6:
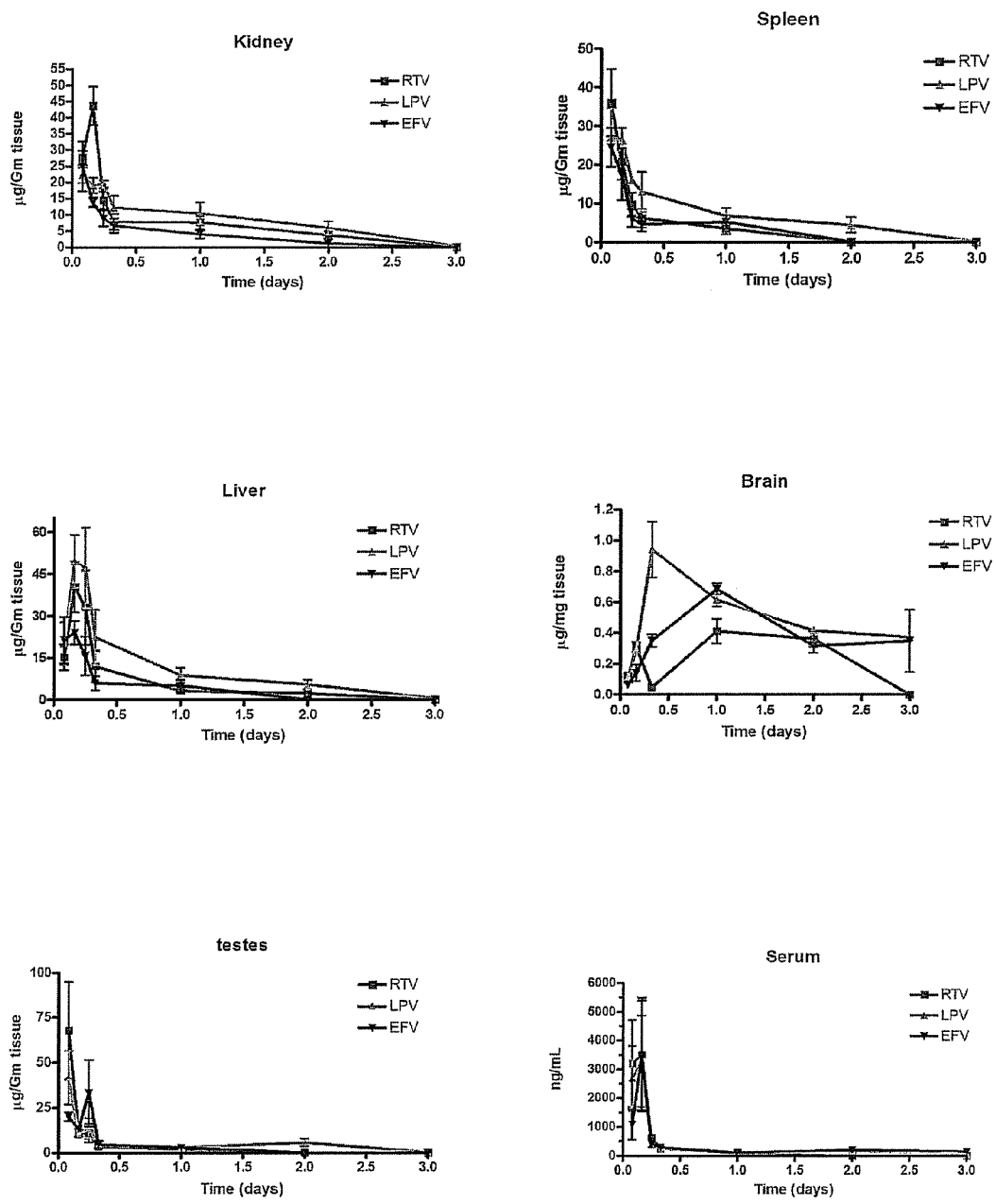
FIG. 6. Concentration vs. time curves for ritonavir, lopinavir, and efavirenz when 500 µg was given as free drugs intraperitoneally as a single dose.

The results of the 500 ug of the combination drugs when given as free drugs are shown from the organs and serum in FIG. 6. Peak antiretroviral drug levels in the serum were found to be at 4 hours post-injection (RTV 3.2±1.5, LPV 3.3±1.6, EFV 3.5±1.9 µg/L). The elimination half-life for each of the drugs was RTV 9.6±2.8, LPV 15.1±6.4, EFV 11.8±2.8 hours. The $AUC_{0-last}$ was calculated by using the trapezoid rule. The AUC for the three drugs were RTV 1398.1±426.7, LPV 1013±901.4, EFV 646±640 ng-day/ml. The volume of distribution (Vd) for the 3 free drugs was RTV 9.7±4.4, LPV 41.6±31.7, EFV 39.3±26.6 L/kg. The antiretroviral drugs were eliminated to non-detectable levels from the majority of tissues by day 3. The exception to this was the brain drug levels were still detectable levels of lopinavir and efavirenz at 3 days post-injection.

Figure 7:
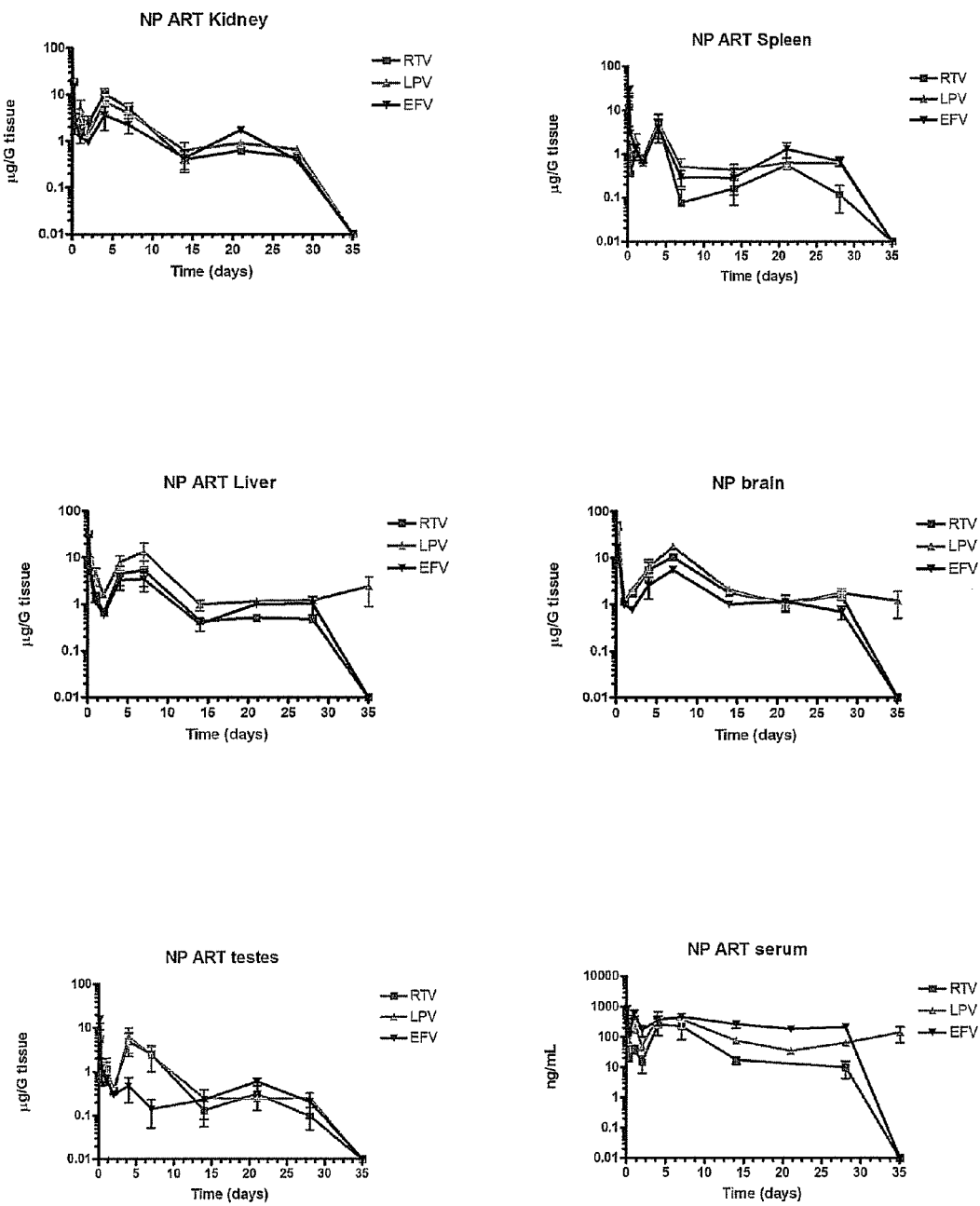
FIG. 7. Concentration vs. time curves for ritonavir, lopinavir, and efavirenz when given as an intraperitoneal 500 µg dose as PLGA nanoparticles.

The results of the 500 µg of the combination drugs when given as the PLGA nanoparticles are shown from the organs and serum in FIG. 7. Peak antiretroviral drug levels in serum were found to be at 0.25 hours post-injection (RTV 339.9±152, LPV 923.2±68.3, EFV 853.2±64.1 ng/ml). The elimination half-life for each of the drugs was also calculated by non-linear regression. Compared to the free drug pharmacokinetics, the elimination half-lives for lopinavir and ritonavir were longer averaging >70 days. The efavirenz mean residence time approached significance (free 0.57±0.25, NP 10.33±4.24 days, p=0.056). Mean residence time for ritonavir and lopinavir when fabricated into the nanoparticle were also longer but not significantly. The Vd and $Cl_T$ for the NPs were (RTV 549.9±360 L/kg, LPV 118.6±165.9 L/kg, EFV 11.38±10.72 L/kg) and (RTV 31.92±26.8 L/d/kg, LPV 4.42±2.03 L/d/kg, EFV 4.1±3.06 L/d/kg), respectively. These pharmacokinetic parameters were not significantly different when compare to those from the free drug. The day 35 levels for the NPs when assayed by HPLC were all less than the detectable limit except lopinavir was found to be detectable in serum, liver, and brain.

The in vitro inhibition of p-24 by the free drugs and NPs were also determined (Table 1). The p-24 ELISA results showed that all three free drugs inhibited p-24 when incubated with HIV individually at an average drug level of 0.1 mg/L. The NPs also inhibited p-24 at a concentration of 0.05 mg/L. These results show that the NPs are able to stay in the tissues of animals for a significantly longer time as compared to free drugs and the NPs release the three antiretrovirals for a minimum of 30 days. Additionally, the released antiretrovirals are able to interact with the HIV virus and inhibit cellular replication.

TABLE 1

Summary of pharmacokinetic parameters for free ART and NP ART

| Parameter | Free ART | NP ART |
|---|---|---|
| $T_{1/2}$ (hrs) | R: 9.6 ± 2.8 | R: 5495.1 ± 9310 |
| | L: 15.1 ± 6.4 | L: 645.3 ± 1013.7 |
| | E: 11.76 ± 2.8 | E: 35.5 ± 20.4 |
| Vd (L/kg) | R: 9.7 ± 4.4 | R: 549.9 ± 360.9 |
| | L: 41.6 ± 37.7 | L: 118.6 ± 165.9 |
| | E: 39.3 ± 26.6 | E: 11.4 ± 10.7 |
| MRT (days) | R: 0.2 ± 0 | R: 32.3 ± 42.4 |
| | L: 0.6 ± 0.34 | L: 228.7 ± 295.9 |
| | E: 0.57 ± 0.25* | E: 10.3 ± 4.24 |
| AUC (ng-day/ml) | R: 1398.1 ± 4579.5 | R: 7020.5 ± 11428.7 |
| | L: 1012.9 ± 901.4 | L: 3329.8 ± 1785.3 |
| | E: 645.9 ± 640.2 | E: 5716.9 ± 3177.7 |

R = ritonavir; L = lopinavir; E = efavirenz; AUC = area under the serum concentration-time curve; MRT = mean residence time within the serum; Vd = volume of distribution; $T_{1/2}$ = elimination half-life;
*p = 0.056 compared to NP drug Discussion The results of these experiments show that the antiretroviral nanoparticles are able to be fabricated to include three antiretroviral drugs. The NPs are able to offer HAART therapy in one IM/SC injection. This has significant ramifications for those who are non-adherent in the United States as this offers another treatment option for these patients. Additionally, this is a treatment option that could be useful for patients affected by HIV the greatest as this type of treatment option may offer the greatest number of patients' continuous treatment in sub-Saharan Africa without oral absorption difficulties. Certainly, there are many patient populations that would find this dosage form useful. The ability to offer this to patients would be advantageous for the HIV community.

Other investigators have also shown that various antiretroviral drugs can be fabricated into a nanoparticle drug delivery system (Dou et al., Blood, 2006, 108:2827-2835, Dou et al., Virology, 2007, 358:148-158, Gorantla et al., J. Leukoc. Biol., 2006, 80:1165-1174, Gagne et al., Biochem. Biophy. Acta, 2002, 1558:198-210, Bender et al., Antimicrob. Agents Chemother., 1996, 40:1467-1471, Kuo Int. J. Pharmaceut., 2005, 290:161-172, Chattopadhyay et al., Pharm. Res., 2008, 25:2262-2271, Mainardes et al., J. Pharm. Sci., 2009, 98:257-267). However, this is the first report of a nanoparticle drug delivery system able to support three antiretroviral drugs in the same nanoparticle. Additionally, the pharmacokinetics of the ART NPs display a wider volume of distribution (Vd) and a longer residence time within the serum (MRT) as compared to the free drugs when administered as an intraperitoneal injection. Based on the results of these experiments, the utility of PLGA ART NPs as a monthly drug delivery system is feasible. The ART NPs allow for serum levels of ritonavir, lopinavir, and efavirenz above the $IC_{50}$ for wild-type virus for a minimum of 30 days.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A particle comprising poly-lactic-co-glycolic acid (PLGA), 4.9% ritonavir, 5.2% lopinavir and 10.8% efavirenz.

2. The particle of claim 1, wherein the particle has an average size of from 10 nanometers to 750 nanometers, and wherein the particle has a surface charge of between −40 mV and −2 mV.

3. The particle of claim 2, wherein the particle has an average size of about 262 nm and a surface charge of about −30 mV.

4. The particle of claim 1, wherein the particle is capable of releasing the ritonavir, the lopinavir and the efavirenz for at least about 28 days after uptake into a cell.

* * * * *